(12) United States Patent
Carter

(10) Patent No.: US 7,863,317 B2
(45) Date of Patent: Jan. 4, 2011

(54) LACTAMS OF ALKYLATED ACYCLIC DIAMINE DERIVATIVES AS MODULATORS OF CHEMOKINE RECEPTOR ACTIVITY

(75) Inventor: Percy H. Carter, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/675,213

(22) Filed: Feb. 15, 2007

(65) Prior Publication Data

US 2007/0197516 A1    Aug. 23, 2007

Related U.S. Application Data

(63) Continuation-in-part of application No. 10/922,726, filed on Aug. 19, 2004, now abandoned.

(51) Int. Cl.
*C07D 207/00* (2006.01)
*A01N 43/36* (2006.01)
(52) U.S. Cl. ....................... 514/424; 548/550
(58) Field of Classification Search .............. None
See application file for complete search history.

(56) References Cited

U.S. PATENT DOCUMENTS

| | | | |
|---|---|---|---|
| 6,136,834 A | 10/2000 | Ohmoto et al. | |
| 6,262,080 B1 | 7/2001 | Warshawsky et al. | |
| 6,706,712 B2 | 3/2004 | Cherney | |
| 2003/0060459 A1 | 3/2003 | Carter et al. | |
| 2003/0216434 A1 | 11/2003 | Cherney | |
| 2004/0186143 A1 | 9/2004 | Carter et al. | |
| 2004/0235835 A1 | 11/2004 | Carter | |
| 2004/0235836 A1 | 11/2004 | Cherney | |

FOREIGN PATENT DOCUMENTS

WO    WO 2005/021499    3/2005

OTHER PUBLICATIONS

U.S. Appl. No. 10/922,406, filed Aug. 19, 2004, Carter et al.
U.S. Appl. No. 10/923,619, filed Aug. 19, 2004, Carter et al.
U.S. Appl. No. 10/923,538, filed Aug. 19, 2004, Carter et al.
U.S. Appl. No. 10/776,828, filed Feb. 11, 2004, Cherney et al.

*Primary Examiner*—Sun Jae Y. Loewe
(74) *Attorney, Agent, or Firm*—Laurelee L. Duncan

(57) ABSTRACT

The present application describes modulators of MCP-1 of formula (I):

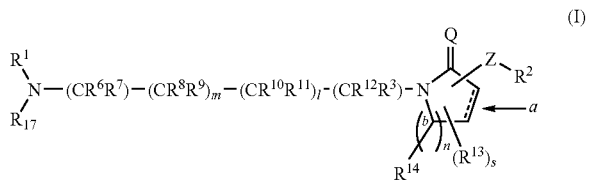

or pharmaceutically acceptable salt forms thereof, useful for the prevention of asthma, multiple sclerosis, artherosclerosis, and rheumatoid arthritis.

2 Claims, No Drawings

LACTAMS OF ALKYLATED ACYCLIC DIAMINE DERIVATIVES AS MODULATORS OF CHEMOKINE RECEPTOR ACTIVITY

CROSS-REFERENCE TO RELATED APPLICATIONS

This application claims benefit to provisional application U.S. Ser. No. 60/497,118 filed Aug. 21, 2003, and is a continuation-in-part of non-provisional application U.S. Ser. No. 10/922,726 filed Aug. 19, 2004. The entire teachings of the referenced application are incorporated herein by reference.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, asthma, rheumatoid arthritis, atherosclerosis, and multiple sclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Luster, New Eng. J. Med. 1998, 338, 436-445 and Rollins, Blood 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (–1 and –2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-trans-membrane-domain proteins (reviewed in: Horuk, Trends Pharm. Sci. 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik and Oshie Immunity 2000, 12, 121): CCR-1 (or "CKR-1" or "CC-CKR-1") [MIP-1α, MCP-3, MCP-4, RANTES] (Ben-Barruch, et al., Cell 1993, 72, 415-425, and Luster, New Eng. J. Med. 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., Proc. Natl. Acad. Sci. USA 1994, 91, 2752-2756, and Luster, New Eng. J. Med. 1998, 338, 436-445); CCR-3 (or "CKR-3" or "CC-CKR-3") [eotaxin-1, eotaxin-2, RANTES, MCP-3, MCP-4] (Combadiere, et al., J. Biol. Chem. 1995, 270, 16491-16494, and Luster, New Eng. J. Med. 1998, 338, 436-445); CCR-4 (or "CKR-4" or "CC-CKR-4") [TARC, MDC] (Power, et al., J. Biol. Chem. 1995, 270, 19495-19500, and Luster, New Eng. J. Med. 1998, 338, 436-445); CCR-5 (or "CKR-5" OR "CC-CKR-5") [MIP-1α, RANTES, MIP-1β] (Sanson, et al., Biochemistry 1996, 35, 3362-3367); CCR-6 (or "CKR-6" or "CC-CKR-6") [LARC] (Baba, et al., J. Biol. Chem. 1997, 272, 14893-14898); CCR-7 (or "CKR-7" or "CC-CKR-7") [ELC] (Yoshie et al., J. Leukoc. Biol. 1997, 62, 634-644); CCR-8 (or "CKR-8" or "CC-CKR-8") [1-309] (Napolitano et al., J. Immunol., 1996, 157, 2759-2763); CCR-10 (or "CKR-10" or "CC-CKR-10") [MCP-1, MCP-3] (Bonini, et al., DNA and Cell Biol. 1997, 16, 1249-1256); and CCR-11 [MCP-1, MCP-2, and MCP-4] (Schweickert, et al., J. Biol. Chem. 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, Curr. Opin. Biotech. 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: P. H. Carter, Current Opinion in Chemical Biology 2002, 6, 510; Trivedi, et al, Ann. Reports Med. Chem. 2000, 35, 191; Saunders and Tarby, Drug Disc. Today 1999, 4, 80; Premack and Schall, Nature Medicine 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, cellular degranulation, and the promotion of leukocyte migration. Demonstration of the importance of the MCP-1/CCR-2 interaction has been provided by experiments with genetically modified mice. MCP-1-/- mice had normal numbers of leukocytes and macrophages, but were unable to recruit monocytes into sites of inflammation after several different types of immune challenge (Bao Lu, et al., J. Exp. Med. 1998, 187, 601). Likewise, CCR-2-/- mice were unable to recruit monocytes or produce interferon-γ when challenged with various exogenous agents; moreover, the leukocytes of CCR-2 null mice did not migrate in response to MCP-1 (Landin Boring, et al., J. Clin. Invest. 1997, 100, 2552), thereby demonstrating the specificity of the MCP-1/CCR-2 interaction. Two other groups have independently reported equivalent results with different strains of CCR-2-/- mice (William A. Kuziel, et al., Proc. Natl. Acad. Sci. USA 1997, 94, 12053, and Takao Kurihara, et al., J. Exp. Med. 1997, 186, 1757). The viability and generally normal health of the MCP-1-/- and CCR-2-/- animals is noteworthy, in that disruption of the MCP-1/CCR-2 interaction does not induce physiological crisis. Taken together, these data lead one to the conclusion that molecules that block the actions of MCP-1 would be useful in treating a number of inflammatory and autoimmune disorders. This hypothesis has now been validated in a number of different animal disease models, as described below.

It is known that MCP-1 is upregulated in patients with rheumatoid arthritis (Alisa Koch, et al., J. Clin. Invest. 1992, 90, 772-779). Moreover, several studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., J. Clin. Invest. 2000, 106, 361). Likewise, inflammatory disease symptoms could be controlled via direct administration of antibodies for MCP-1 to rats with collagen-induced arthritis (Hiroomi Ogata, et al., J. Pathol. 1997, 182, 106), or streptococcal cell wall-induced arthritis (Ralph C. Schimmer, et al., J. Immunol. 1998, 160, 1466). Perhaps most significantly, a peptide antagonist of MCP-1, MCP-1 (9-76), was shown both to prevent disease onset and to reduce disease symptoms (depending on the time of administration) in the MRL-lpr mouse model of arthritis (Jiang-Hong Gong, et al., J. Exp. Med. 1997, 186, 131).

It is known that MCP-1 is upregulated in atherosclerotic lesions, and it has been shown that circulating levels of MCP-1 are reduced through treatment with therapeutic agents, plays a role in disease progression (Abdolreza Rezaie-Majd, et al, Arterioscler. Thromb. Vasc. Biol. 2002, 22, 1194-1199). Four key studies have demonstrated the potential therapeutic value of antagonism of the MCP-1/CCR2 interaction in treating atherosclerosis. For example, when MCP-1−/− mice are mated with LDL receptor-deficient mice, an 83% reduction in aortic lipid deposition was observed (Long Gu, et al., Mol. Cell. 1998, 2, 275). Similarly, when MCP-1 was genetically ablated from mice which already overexpressed human apolipoprotein B, the resulting mice were protected from atherosclerotic lesion formation relative to the MCP-1+/+apoB control mice (Jennifa Gosling, et al., J. Clin. Invest. 1999, 103, 773). Likewise, when CCR-2−/− mice are crossed with apolipoprotein E −/− mice, a significant decrease in the incidence of atherosclerotic lesions was observed (Landin Boring, et al, Nature 1998, 394, 894). Finally, when apolipoprotein E −/− mice are administered a gene encoding a peptide antagonist of CCR2, then lesion size is decreased and plaque stability is increased (W. Ni, et al. Circulation 2001, 103, 2096-2101).

It is known that MCP-1 is upregulated in human multiple sclerosis, and it has been shown that effective therapy with interferon b-1b reduces MCP-1 expression in peripheral blood mononuclear cells, suggesting that MCP-1 plays a role in disease progression (Carla Iarlori, et al., J. Neuroimmunol. 2002, 123, 170-179). Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple scelerosis. Administration of antibodies for MCP-1 to animals with EAE significantly diminished disease relapse (K. J. Kennedy, et al., J. Neuroimmunol. 1998, 92, 98). Furthermore, two recent reports have now shown that CCR-2−/− mice are resistant to EAE (Brian T. Fife, et al., J. Exp. Med. 2000, 192, 899; Leonid Izikson, et al., J. Exp. Med. 2000, 192, 1075).

It is known that MCP-1 is upregulated in patients who develop bronchiolitis obliterans syndrome after lung transplantation (Martine Reynaud-Gaubert, et al., J. of Heart and Lung Transplant., 2002, 21, 721-730; John Belperio, et al., J. Clin. Invest. 2001, 108, 547-556). In a murine model of bronchiolitis obliterans syndrome, administration of an antibody to MCP-1 led to attenuation of airway obliteration; likewise, CCR2−/− mice were resistant to airway obliteration in this same model (John Belperio, et al., J. Clin. Invest. 2001, 108, 547-556). These data suggest that antagonism of MCP-1/CCR2 may be beneficial in treating rejection of organs following transplantation.

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., J. Exp. Med. 1998, 188, 157). It proved possible to reduce allergic airway inflammation in Schistosoma mansoni egg-challenged mice through the administration of antibodies for MCP-1 (Nicholas W. Lukacs, et al., J. Immunol. 1997, 158, 4398). Consistent with this, MCP-1−/− mice displayed a reduced response to challenge with Schistosoma mansoni egg (Bao Lu, et al., J. Exp. Med. 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., J. Exp. Med. 1997, 185, 1371). In addition, MCP-1−/− mice with induced nephrotoxic serum nephritis showed significantly less tubular damage than their MCP-1+/+counterparts (Gregory H. Tesch, et al., J. Clin. Invest. 1999, 103, 73).

One study has demonstrated the potential therapeutic value of antagonism of the MCP-1/CCR2 interaction in treating systemic lupus erythematosus. Crossing of MCP-1−/− mice with MRL-FAS$^{lpr}$ mice—the latter of which have a fatal autoimmune disease that is analogous to human systemic lupus erythematosus—results mice that have less disease and longer survival than the wildtype MRL-FAS$^{lpr}$ mice (Gregory H. Tesch, et al., J. Exp. Med. 1999, 190, 1813).

One study has demonstrated the potential therapeutic value of antagonism of the MCP-1/CCR2 interaction in treating colitis. CCR-2−/− mice were protected from the effects of dextran sodium sulfate-induced colitis (Pietro G. Andres, et al., J. Immunol. 2000, 164, 6303).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Michael L. Jones, et al., J. Immunol. 1992, 149, 2147).

One study has demonstrated the potential therapeutic value of antagonism of the MCP-1/CCR2 interaction in treating cancer. When immunodeficient mice bearing human breast carcinoma cells were treated with an anti-MCP-1 antibody, inhibition of lung micrometastases and increases in survival were observed (Rosalba Salcedo, et al., Blood 2000, 96, 34-40).

One study has demonstrated the potential therapeutic value of antagonism of the MCP-1/CCR2 interaction in treating restinosis. Mice deficient in CCR2 showed reductions in the intimal area and in the intima/media ratio (relative to wildtype littermates) after injury of the femoral artery (Merce Roque, et al. Arterioscler. Thromb. Vasc. Biol. 2002, 22, 554-559).

Other studies have provided evidence that MCP-1 is overexpressed in various disease states not mentioned above. These reports provide correlative evidence that MCP-1 antagonists could be useful therapeutics for such diseases. Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804). Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). Another study has demonstrated the overexpression of MCP-1 in rodent cardiac allografts, suggesting a role for MCP-1 in the pathogenesis of transplant arteriosclerosis (Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127). Finally, a recent report has shown that MCP-1 is overexpressed in the brains and cerebrospinal fluid of patients with HIV-1-associated dementia (Alfredo Garzino-Demo, WO 99/46991).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR-2 is also the receptor for the chemokines MCP-2, MCP-3, MCP-4, and MCP-5 (Luster, *New Eng. J. Med.* 1998, 338, 436-445). Since it is presumed that the new compounds of formula (I) described herein antagonize MCP-1 by binding to the CCR-2 receptor, it may be that these compounds of formula (I) are also effective antagonists of the actions of MCP-2, MCP-3, MCP-4, and MCP-5 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis, multiple sclerosis, and atherosclerosis, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

These and other features of the invention, which will become apparent during the following detailed description, have been achieved by the inventors' discovery that compounds of formula (I):

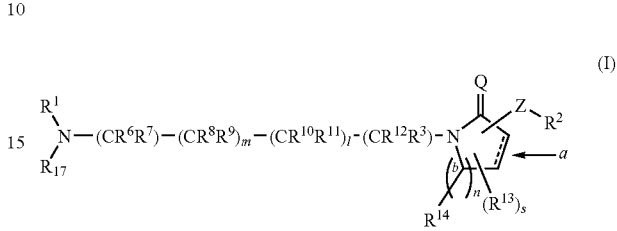

or stereoisomers or pharmaceutically acceptable salts thereof, wherein Q, Z, m, n, l, s, carbon atom (b), bond (a) $R^1$, $R^2$, $R^3$, $R^6$, $R^7$, $R^8$, $R^9$, $R^{10}$, $R^{11}$, $R^{12}$, $R^{13}$, $R^{14}$, and $R^{17}$, are defined below, are effective modulators of chemokine activity.

DETAILED DESCRIPTION OF EMBODIMENTS OF THE PRESENT INVENTION

Thus, in one embodiment, the present invention provides novel compounds of formula (I):

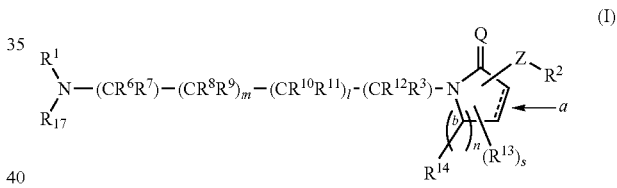

or a stereoisomer or a pharmaceutically acceptable salt thereof, wherein:

Z is selected from a bond, —$NR^{18}C(O)$—, —$NR^{18}C(S)$—, —$NR^{18}C(O)NH$—, —$NR^{18}C(S)NH$—, —$NR^{18}SO_2$—, —$NR^{18}SO_2NH$—, —$C(O)NR^{18}$—, —$OC(O)NR^{18}$—, —$NR^{18}C(O)O$—, —$(CR^{25}R^{25})_r$—, —$CR^{24}$=$CR^{24}$—, —$CR^{25}R^{25}C(O)$—, —$C(O)CR^{25}R^{25}$—, —$CR^{25}R^{25}C$(=N—$OR^{26}$)—, —O—$CR^{24}R^{24}$—, —$CR^{24}R^{24}$—O—, —O—, —$NR^{19}$—, —$NR^{19}$—$CR^{24}R^{24}$—, —$CHR^{24}$—$NR^{19}$—, —$S(O)_p$—, —$S(O)_p$—$CR^{24}R^{24}$—, and —$S(O)_p$—$NR^{19}$—;

Q is selected from O or S;

wherein neither Z nor $R^{13}$ are connected to a carbon atom labeled (b);

bond (a) is a single or double bond;

alternatively, when n is equal to 2, two atoms labeled (b) may join through a double bond;

$R^1$ is selected from H, $C_{1-6}$ alkyl substituted with 0-3 $R^4$, $C_{2-6}$ alkenyl substituted with 0-3 $R^4$, $C_{2-6}$ alkynyl substituted with 0-3 $R^4$, $R^2$ is selected from a $C_{6-10}$ aryl group substituted with 0-5 $R^5$ and a 5-10 membered heteroaryl system containing 1-4 heteroatoms selected from N, O, and S, substituted with 0-3 $R^5$;

$R^3$ is selected from H, $(CRR)_q OH$, $(CRR)_q SH$, $(CRR)_q OR^{3d}$, $(CRR)_q S(O)_p R^{3d}$, $(CRR)_r C(O)R^{3b}$, $(CRR)_q NR^{3a}R^{3a}$, $(CRR)_r C(O)NR^{3a}R^{3a}$, $(CRR)_r C(O)NR^{3a}OR^{3d}$, $(CRR)_q SO_2 NR^{3a}R^{3a}$, $(CRR)_r C(O)OR^{3d}$, a $(CRR)_r$—$C_{3-10}$ carbocyclic residue substituted with 0-5 $R^{3e}$, and a $(CRR)_r$-5-10 membered heterocyclic system containing 1-4 heteroatoms selected from N, O, and S, substituted with 0-3 $R^{3e}$;

with the proviso that $R^3$ is not H if $R^6$ is H;

alternatively, $R^3$ and $R^{12}$ join to form a $C_{3-6}$ cycloalkyl substituted with 0-2 $R^{3g}$, a 5-6 membered lactam ring in which carbon atoms of the ring are substituted with 0-2 $R^{3g}$, or a 5-6 membered lactone ring in which carbon atoms of the ring are substituted with 0-2 $R^{3g}$;

$R^{3a}$, at each occurrence, is independently selected from H, methyl substituted with 0-1 $R^{3c}$, $C_{2-6}$ alkyl substituted with 0-3 $R^{3e}$, $C_{3-8}$ alkenyl substituted with 0-3 $R^{3e}$, $C_{3-8}$ alkynyl substituted with 0-3 $R^{3e}$, $(CH_2)_r C_{3-6}$ cycloalkyl, a $(CH_2)_r$—$C_{3-10}$ carbocyclic residue substituted with 0-5 $R^{3e}$, and a $(CH_2)_r$-5-10 membered heterocyclic system containing 1-4 heteroatoms selected from N, O, and S, substituted with 0-3 $R^{3e}$;

$R^{3b}$, at each occurrence, is independently selected from $C_{1-6}$ alkyl substituted with 0-3 $R^{3e}$, $C_{2-8}$ alkenyl substituted with 0-3 $R^{3e}$, $C_{2-8}$ alkynyl substituted with 0-3 $R^{3e}$, a $(CH_2)_r$—$C_{3-6}$ carbocyclic residue substituted with 0-2 $R^{3e}$, and a $(CH_2)_r$-5-6 membered heterocyclic system containing 1-4 heteroatoms selected from N, O, and S, substituted with 0-3 $R^{3e}$;

$R^{3c}$ is independently selected from —$C(O)R^{3b}$, —$C(O)OR^{3d}$, —$C(O)NR^{3f}R^{3f}$, and $(CH_2)_r$phenyl;

$R^{3d}$, at each occurrence, is independently selected from H, methyl, —$CF_3$, $C_{2-6}$ alkyl substituted with 0-3 $R^{3e}$, $C_{3-6}$ alkenyl substituted with 0-3 $R^{3e}$, $C_{3-6}$ alkynyl substituted with 0-3 $R^{3e}$, a $C_{3-10}$ carbocyclic residue substituted with 0-3 $R^{3e}$, and a $(CH_2)_r$-5-6 membered heterocyclic system containing 1-4 heteroatoms selected from N, O, and S, substituted with 0-3 $R^{3e}$;

$R^{3e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{3f}R^{3f}$, $(CH_2)_r C(O)NHR^{3h}$, $(CH_2)_r OC(O)NHR^{3h}$, $(CH_2)_r OH$, $(CH_2)_r C(O)OH$, $(CH_2)_r C(O)OR^{3h}$, $(CH_2)_r C(O)NHSO_2$—$R^{3h}$, $NHSO_2 R^{3h}$, a $(CH_2)_r$-5-6 membered heterocyclic system containing 1-4 heteroatoms selected from N, O, and S, and $(CH_2)_r$phenyl;

$R^{3f}$, at each occurrence, is selected from H, $C_{1-6}$ alkyl, and $C_{3-6}$ cycloalkyl;

$R^{3g}$ is selected from $(CHR)_r OH$, $(CHR)_r SH$, $(CHR)_r OR^{3d}$, $(CHR)_r S(O)_p R^{3d}$, $(CHR)_r C(O)R^{3b}$, $(CHR)_r NR^{3a}R^{3a}$, $(CHR)_r C(O)NR^{3a}R^{3a}$, $(CHR)_r C(O)NR^{3a}OR^{3d}$, $(CHR)_r SO_2 NR^{3a}R^{3a}$, $(CHR)_r C(O)OR^{3d}$, and a $(CHR)_r$—$C_{3-10}$ carbocyclic residue substituted with 0-5 $R^{3e}$;

$R^{3h}$, at each occurrence, is selected from $C_{1-5}$ alkyl, $C_{1-5}$ haloalkyl, and $C_{3-6}$ cycloalkyl, and phenyl;

R, at each occurrence, is independently selected from H, $C_{1-6}$ alkyl substituted with 0-3 $R^{3e}$, $C_{2-8}$ alkenyl substituted with 0-3 $R^{3e}$, $C_{2-8}$ alkynyl substituted with 0-3 $R^{3e}$, $(CH_2)_r C_{3-6}$ cycloalkyl, $(CH_2)_r C(O)NR^{3a}R^{3a}$, and $(CH_2)_r C(O)OR^{3d}$, $(CH_2)S(O)_2 R^{3d}$, and $(CH_2)_r$phenyl substituted with 0-3 $R^{3e}$, and a $(CH_2)_r$-5-10 membered heterocyclic system containing 1-4 heteroatoms selected from N, O, and S, substituted with 0-3 $R^{3e}$;

$R^4$, at each occurrence, is selected from $C_{1-8}$ alkyl, $C_{2-8}$ alkenyl, $C_{2-8}$ alkynyl, $(CH_2)_r C_{3-6}$ cycloalkyl substituted with 0-3 $R^{4e}$, Cl, Br, I, F, $NO_2$, CN, $(CR'R')_q NR^{4a}R^{4a}$, $(CR'R')_q OH$, $(CR'R')_q O(CR'R')_r R^{4d}$ $(CR'R')_q SH$, $(CR'R')_r C(O)H$, $(CR'R')_q S(CR'R')_r R^{4d}$, $(CR'R')_r C(O)OH$, $(CR'R')_r C(O)(CR'R')_r R^{4b}$, $(CR'R')_r C(O)NR^{4a}R^{4a}$, $(CR'R')_q NR^{4f}C(O)(CR'R')_r R^{4b}$, $(CR'R')_r C(O)O (CR'R')_r R^{4d}$, $(CR'R')_q OC(O)(CR'R')_r R^{4b}$, $(CR'R')_q NR^{4f}C(O)O(CR'R')_r R^{4d}$, $(CR'R')_q OC(O)NR^{4a}R^{4a}$, $(CR'R')_q NR^{4a}C(S)NR^{4a}(CR'R')_r R^{4d}$, $(CR'R')_q NR^{4a}C(O) NR^{4a}R^{4a}$, $(CR'R')_r C(=NR^{4f})NR^{4a}R^{4a}$, $(CR'R')_q NHC(=NR^{4f})NR^{4f}R^{4f}$, $(CR'R')_r S(O)_p (CR'R')_r R^{4b}$, $(CR'R')_r S(O)_2 NR^{4a}R^{4a}$, $(CR'R')_q NR^{4f}S(O)_2 NR^{4a}R^{4a}$, $(CR'R')_q NR^{4f}S(O)_2 (CR'R')_r R^{4b}$, $C_{1-6}$ haloalkyl, $C_{2-8}$ alkenyl substituted with 0-3 R', $C_{2-8}$ alkynyl substituted with 0-3 R', and a $(CR'R')_r$nonaromatic-heterocycle containing 1-4 heteroatoms substituted with 0-3 $R^{4e}$;

alternatively, two $R^4$ on adjacent atoms on $R^1$ may join to form a cyclic acetal;

$R^{4a}$, at each occurrence, is independently selected from H, methyl substituted with 0-1$R^{4g}$, $C_{2-6}$ alkyl substituted with 0-2 $R^{4e}$, $C_{3-8}$ alkenyl substituted with 0-2 $R^{4e}$, $C_{3-8}$ alkynyl substituted with 0-2 $R^{4e}$, a $(CH_2)_r$—$C_{3-10}$ cycloalkyl residue substituted with 0-5 $R^{4e}$, and a $(CH_2)_r$-5-10 membered nonaromatic heterocyclic system containing 1-4 heteroatoms selected from N, O, and S, substituted with 0-2 $R^{4e}$;

$R^{4b}$, at each occurrence, is selected from $C_{1-6}$ alkyl substituted with 0-2 $R^{4e}$, $C_{3-8}$ alkenyl substituted with 0-2 $R^{4e}$, $C_{3-8}$ alkynyl substituted with 0-2 $R^{4e}$, a $(CH_2)_r C_{3-6}$ cycloalkyl residue substituted with 0-3 $R^{4e}$, and a $(CH_2)_r$-5-6 membered nonaromatic heterocyclic system containing 1-4 heteroatoms selected from N, O, and S, substituted with 0-2 $R^{4e}$;

$R^{4d}$, at each occurrence, is selected from $C_{3-8}$ alkenyl substituted with 0-2 $R^{4e}$, $C_{3-8}$ alkynyl substituted with 0-2 $R^{4e}$, methyl, $CF_3$, $C_{2-6}$ alkyl substituted with 0-3 $R^{4e}$, a $(CH_2)_r$—$C_{3-10}$ cycloalkyl residue substituted with 0-3 $R^{4e}$, and a $(CH_2)_r$-5-6 membered nonaromatic heterocyclic system containing 1-4 heteroatoms selected from N, O, and S, substituted with 0-3 $R^{4e}$;

$R^{4e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, and $(CH_2)_r NR^{4f}R^{4f}$;

$R^{4f}$, at each occurrence, is selected from H, $C_{1-5}$ alkyl, and $C_{3-6}$ cycloalkyl, and phenyl;

$R^{4g}$ is independently selected from —$C(O)R^{4b}$, —$C(O)OR^{4d}$, and —$C(O)NR^{4f}R^{4f}$;

$R^5$, at each occurrence, is selected from $C_{1-8}$ alkyl, $C_{2-8}$ alkenyl, $C_{2-8}$ alkynyl, $(CH_2)_r C_{3-6}$ cycloalkyl, Cl, Br, I, F, $NO_2$, CN, $(CR'R')_r NR^{5a}R^{5a}$, $(CR'R')_r OH$, $(CR'R')_r O (CR'R')_r R^{5d}$, $(CR'R')_r SH$, $(CR'R')_r C(O)H$, $(CR'R')_r S (CR'R')_r R^{5d}$, $(CR'R')_r C(O)OH$, $(CR'R')_r C(O)(CR'R')_r R^{5b}$, $(CR'R')_r C(O)NR^{5a}R^{5a}$, $(CR'R')_r NR^{5f}C(O)(CR'R')_r R^{5b}$, $(CR'R')_r C(O)O(CR'R')_r R^{5d}$, $(CR'R')_r OC(O)(CR'R')_r R^{5b}$, $(CR'R')_r NR^{5f}C(O)O(CR'R')_r R^{5d}$, $(CR'R')_r OC(O)NR^{5a}R^{5a}$, $(CR'R')_r NR^{5a}C(O)NR^{5a}R^{5a}$, $(CR'R')_r C(=NR^{5f})NR^{5a}R^{5a}$, $(CR'R')_r NHC(=NR^{5f})NR^{5f}R^{5f}$, $(CR'R')_r S(O)_p (CR'R')_r R^{5b}$, $(CR'R')_r S(O)_2 NR^{5a}R^{5a}$, $(CR'R')_r NR^{5a}S (O)_2 NR^{5a}R^{5a}$, $(CR'R')_r NR^{5f}S(O)_2 (CR'R')_r R^{5b}$, $C_{1-6}$ haloalkyl, $C_{2-8}$ alkenyl substituted with 0-3 R', $C_{2-8}$ alkynyl substituted with 0-3 R', $(CR'R')_r C_{3-10}$ carbocycle substituted with 0-3 $R^{5e}$, $(CR'R')_r$phenyl substituted with 0-3 $R^{5e}$, and a $(CR'R')_r$-5-10 membered heterocyclic system containing 1-4 heteroatoms selected from N, O, and S, substituted with 0-2 $R^{5e}$;

alternatively, two $R^5$ on adjacent atoms on $R^2$ may join to form a cyclic acetal;

$R^{5a}$, at each occurrence, is independently selected from H, methyl substituted with 0-1 $R^{5g}$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-10}$ carbocyclic residue substituted with 0-5 $R^{5e}$, and a $(CH_2)_r$-5-10 membered heterocyclic system containing 1-4 heteroatoms selected from N, O, and S, substituted with 0-2 $R^{5e}$;

$R^{5b}$, at each occurrence, is independently selected from $C_{1-6}$ alkyl substituted with 0-3 $R^{5e}$, $C_{1-6}$ haloalkyl, $C_{3-8}$ alkenyl substituted with 0-2 $R^{5e}$, $C_{3-8}$ alkynyl substituted with 0-2 $R^{5e}$, a $(CH_2)_rC_{3-6}$ carbocyclic residue substituted with 0-3 $R^{5e}$, and a $(CH_2)_r$-5-6 membered heterocyclic system containing 1-4 heteroatoms selected from N, O, and S, substituted with 0-2 $R^{5e}$;

$R^{5d}$, at each occurrence, is independently selected from $C_{3-8}$ alkenyl substituted with 0-2 $R^{5e}$, $C_{3-8}$ alkynyl substituted with 0-2 $R^{5e}$, methyl, $CF_3$, $C_{2-6}$ alkyl substituted with 0-3 $R^{5e}$, a $(CH_2)_r$—$C_{3-10}$ carbocyclic residue substituted with 0-3 $R^{5e}$, and a $(CH_2)_r$-5-6 membered heterocyclic system containing 1-4 heteroatoms selected from N, O, and S, substituted with 0-3 $R^{5e}$;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, $(CH_2)_rOH$, OH, SH, C(O)OH, C(O)NHR$^{5h}$, C(O)OC$_{1-5}$ alkyl, $(CH_2)_rSC_{1-5}$ alkyl, $(CH_2)_rNR^{5f}R^{5f}$, $(CH_2)_rC(O)NHSO_2$—$R^{5h}$, $NHSO_2R^{5h}$, and $(CH_2)_r$phenyl, $(CH_2)_r$tetrazolyl;

$R^{5f}$, at each occurrence, is selected from H, $C_{1-5}$ alkyl, and $C_{3-6}$ cycloalkyl, and phenyl;

$R^{5g}$ is independently selected from —C(O)$R^{5b}$, —C(O)OR$^{5d}$, —C(O)NR$^{5f}R^{5f}$, and $(CH_2)_r$phenyl;

$R^{5h}$, at each occurrence, is selected from $C_{1-5}$ alkyl, $C_{1-5}$ haloalkyl, and $C_{3-6}$ cycloalkyl, and phenyl;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, is selected from H, $C_{1-6}$ alkyl, $C_{2-6}$ alkenyl, $C_{2-6}$ alkynyl, $(CRR)_qOH$, $(CRR)_qSH$, $(CRR)_qOR^{6d}$, $(CRR)_qS(O)_pR^{6d}$, $(CRR)_rC(O)R^{6b}$, $(CRR)_rNR^{6a}R^{6a}$, $(CRR)_rC(O)NR^{6a}R^{6a}$, $(CRR)_rC(O)NR^{6a}OR^{6d}$, $(CRR)SO_2NR^{6a}R^{6a}$, $(CRR)_rC(O)OR^{6d}$, a $(CRR)_r$—$C_{3-10}$ carbocyclic residue substituted with 0-5 $R^{6e}$, and a $(CRR)_r$-5-10 membered heterocyclic system containing 1-4 heteroatoms selected from N, O, and S, substituted with 0-3 $R^{6e}$;

alternatively, $R^6$ and $R^7$ join to form a $C_{3-6}$ cycloalkyl substituted with 0-2 $R^{6g}$, a 5-6 membered ring lactam substituted with 0-2 $R^{6g}$, or a 5-6 membered ring lactone substituted with 0-2 $R^{6g}$;

$R^{6a}$, at each occurrence, is independently selected from H, methyl, $C_{2-6}$ alkyl substituted with 0-3 $R^{6e}$, $C_{3-8}$ alkenyl substituted with 0-3 $R^{6e}$, $C_{3-8}$ alkynyl substituted with 0-3 $R^{6e}$, $(CH_2)_rC_{3-6}$ cycloalkyl, a $(CH_2)_r$—$C_{3-10}$ carbocyclic residue substituted with 0-5 $R^{6e}$, and a $(CH_2)_r$-5-10 membered heterocyclic system containing 1-4 heteroatoms selected from N, O, and S, substituted with 0-3 $R^{6e}$;

$R^{6b}$, at each occurrence, is independently selected from $C_{1-6}$ alkyl substituted with 0-3 $R^{6e}$, $C_{2-8}$ alkenyl substituted with 0-3 $R^{6e}$, $C_{2-8}$ alkynyl substituted with 0-3 $R^{6e}$, a $(CH_2)_r$—$C_{3-6}$ carbocyclic residue substituted with 0-2 $R^{6e}$, and a $(CH_2)_r$-5-6 membered heterocyclic system containing 1-4 heteroatoms selected from N, O, and S, substituted with 0-3 $R^{6e}$;

$R^{6d}$, at each occurrence, is independently selected from H, methyl, —$CF_3$, $C_{2-6}$ alkyl substituted with 0-3 $R^{6e}$, $C_{3-6}$ alkenyl substituted with 0-3 $R^{6e}$, $C_{3-6}$ alkynyl substituted with 0-3 $R^{6e}$, a $C_{3-10}$ carbocyclic residue substituted with 0-3 $R^{6e}$, and a $(CH_2)_r$-5-6 membered heterocyclic system containing 1-4 heteroatoms selected from N, O, and S, substituted with 0-3 $R^{6e}$;

$R^{6e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-16}$ alkyl, SH, $(CH_2)_rSC_{1-5}$ alkyl, $(CH_2)_rNR^{6f}R^{6f}$, and $(CH_2)_r$phenyl;

$R^{6f}$, at each occurrence, is independently selected from H, $C_{1-6}$ alkyl, and $C_{3-6}$ cycloalkyl;

$R^{6g}$ is selected from $(CHR)_qOH$, $(CHR)_qSH$, $(CHR)_qOR^{6d}$, $(CHR)_qS(O)_pR^{6d}$, $(CHR)_rC(O)R^{6b}$, $(CHR)_qNR^{6a}R^{6a}$, $(CHR)_rC(O)NR^{6a}R^{6a}$, $(CHR)_rC(O)NR^{6a}OR^{6d}$, $(CHR)_qSO_2NR^{6a}R^{6a}$, $(CHR)_rC(O)OR^{6d}$, and a (CHR) r-$C_{3-10}$ carbocyclic residue substituted with 0-5 $R^{6e}$;

$R^7$, is selected from H, $C_{1-6}$ alkyl, $C_{2-6}$ alkenyl, $C_{2-6}$ alkynyl, $(CRR)_qOH$, $(CRR)_qSH$, $(CRR)_qOR^{7d}$, $(CRR)_qS(O)_pR^{7d}$, $(CRR)_rC(O)R^{7b}$, $(CRR)_rNR^{7a}R^{7a}$, $(CRR)_rC(O)NR^{7a}R^{7a}$, $(CRR)_rC(O)NR^{7a}OR^{7d}$, $(CRR)_qSO_2NR^{7a}R^{7a}$, $(CRR)_rC(O)OR^{7d}$, a $(CRR)_r$—$C_{3-10}$ carbocyclic residue substituted with 0-5 $R^{7e}$, and a $(CRR)_r$-5-10 membered heterocyclic system containing 1-4 heteroatoms selected from N, O, and S, substituted with 0-3 $R^{7e}$;

$R^{7a}$, at each occurrence, is independently selected from H, methyl, $C_{2-6}$ alkyl substituted with 0-3 $R^{7e}$, $C_{3-8}$ alkenyl substituted with 0-3 $R^{7e}$, $C_{3-8}$ alkynyl substituted with 0-3 $R^{7e}$, $(CH_2)_rC_{3-6}$ cycloalkyl, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-3 $R^{7e}$;

$R^{7b}$, at each occurrence, is independently selected from $C_{1-6}$ alkyl substituted with 0-3 $R^{7e}$, $C_{2-8}$ alkenyl substituted with 0-3 $R^{7e}$, $C_{2-8}$ alkynyl substituted with 0-3 $R^{7e}$, a $(CH_2)_r$—$C_{3-6}$ carbocyclic residue substituted with 0-2 $R^{7e}$, and a $(CH_2)_r$-5-6 membered heterocyclic system containing 1-4 heteroatoms selected from N, O, and S, substituted with 0-3 $R^{7e}$;

$R^{7d}$, at each occurrence, is independently selected from H, methyl, —$CF_3$, $C_{2-6}$ alkyl substituted with 0-3 $R^{7e}$, $C_{3-6}$ alkenyl substituted with 0-3 $R^{7e}$, $C_{3-6}$ alkynyl substituted with 0-3 $R^{7e}$, a $C_{3-10}$ carbocyclic residue substituted with 0-3 $R^{7e}$, and a $(CH_2)_r$-5-6 membered heterocyclic system containing 1-4 heteroatoms selected from N, O, and S, substituted with 0-3 $R^{7e}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{7f}R^{7f}$, and $(CH_2)_r$phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{8d}$, $(CRR)_rS(O)_pR^{8d}$, $(CRR)_rC(O)R^{8b}$, $(CRR)_rNR^{8a}R^{8a}$, $(CRR)_rC(O)NR^{8a}R^{8a}$, $(CRR)_rC(O)NR^{8a}OR^{8d}$, $(CRR)_rSO_2NR^{8a}R^{8a}$, $(CRR)_rC(O)OR^{8d}$, a $(CRR)_r$—$C_{3-10}$ carbocyclic residue substituted with 0-5 $R^{8e}$, and a $(CRR)_r$-5-10 membered heterocyclic system containing 1-4 heteroatoms selected from N, O, and S, substituted with 0-3 $R^{8e}$;

alternatively, $R^8$ and $R^9$ join to form a $C_{3-6}$ cycloalkyl substituted with 0-2 $R^{8g}$, a 5-6 membered ring lactam substituted with 0-2 $R^{8g}$, or a 5-6 membered ring lactone substituted with 0-2 $R^{8g}$;

$R^{8a}$, at each occurrence, is independently selected from H, methyl, $C_{2-6}$ alkyl substituted with 0-3 $R^{8e}$, $C_{3-8}$ alkenyl substituted with 0-3 $R^{8e}$, $C_{3-8}$ alkynyl substituted with 0-3 $R^{8e}$, $(CH_2)_rC_{3-6}$ cycloalkyl, a $(CH_2)_r$—$C_{3-10}$ carbocyclic residue substituted with 0-5 $R^{8e}$, and a $(CH_2)_r$-5-10 membered heterocyclic system containing 1-4 heteroatoms selected from N, O, and S, substituted with 0-3 $R^{8e}$;

$R^{8b}$, at each occurrence, is independently selected from $C_{1-6}$ alkyl substituted with 0-3 $R^{8e}$, $C_{2-8}$ alkenyl substituted with 0-3 $R^{8e}$, $C_{2-8}$ alkynyl substituted with 0-3 $R^{8e}$, a $(CH_2)_r$—$C_{3-6}$ carbocyclic residue substituted with 0-2 $R^{8e}$, and a $(CH_2)_r$-5-6 membered heterocyclic system containing 1-4 heteroatoms selected from N, O, and S, substituted with 0-3 $R^{8e}$;

$R^{8d}$, at each occurrence, is independently selected from H, methyl, —$CF_3$, $C_{2-6}$ alkyl substituted with 0-3 $R^{8e}$, $C_{3-6}$ alkenyl substituted with 0-3 $R^{8e}$, $C_{3-6}$ alkynyl substituted with 0-3 $R^{8e}$, a $C_{3-10}$ carbocyclic residue substituted with 0-3 $R^{8e}$, and a $(CH_2)_r$-5-6 membered heterocyclic system containing 1-4 heteroatoms selected from N, O, and S, substituted with 0-3 $R^{8e}$;

$R^{8e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{8f}R^{8f}$, and $(CH_2)_r$phenyl;

$R^{8f}$, at each occurrence, is independently selected from H, $C_{1-6}$ alkyl, and $C_{3-6}$ cycloalkyl;

$R^{8g}$ is selected from $(CHR)_qOH$, $(CHR)_qSH$, $(CHR)_qOR^{8d}$, $(CHR)_qS(O)_pR^{8d}$, $(CHR)_rC(O)R^{8b}$, $(CHR)_qNR^{8a}R^{8a}$, $(CHR)_rC(O)NR^{8a}R^{8a}$, $(CHR)_rC(O)NR^{8a}OR^{8d}$, $(CHR)_qSO_2NR^{8a}R^{8a}$, $(CHR)_rC(O)OR^{8d}$, and a $(CHR)_r$—$C_{3-10}$ carbocyclic residue substituted with 0-5 $R^{8e}$;

$R^9$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{9d}$, $(CRR)_rS(O)_pR^{9d}$, $(CRR)_rC(O)R^{9b}$, $(CRR)_rNR^{9a}R^{9a}$, $(CRR)_rC(O)NR^{9a}R^{9a}$, $(CRR)_rC(O)NR^{9a}OR^{9d}$, $(CRR)_rSO_2NR^{9a}R^{9a}$, $(CRR)_rC(O)OR^{9d}$, a $(CRR)_r$—$C_{3-10}$ carbocyclic residue substituted with 0-5 $R^{9e}$, and a $(CRR)_r$-5-10 membered heterocyclic system containing 1-4 heteroatoms selected from N, O, and S, substituted with 0-3 $R^{9e}$;

$R^{9a}$, at each occurrence, is independently selected from H, methyl, $C_{2-6}$ alkyl substituted with 0-3 $R^{9e}$, $C_{3-8}$ alkenyl substituted with 0-3 $R^{9e}$, $C_{3-8}$ alkynyl substituted with 0-3 $R^{9e}$, $(CH_2)_rC_{3-6}$ cycloalkyl, a $(CH_2)_r$—$C_{3-10}$ carbocyclic residue substituted with 0-5 $R^{9e}$, and a $(CH_2)_r$-5-10 membered heterocyclic system containing 1-4 heteroatoms selected from N, O, and S, substituted with 0-3 $R^{9e}$;

$R^{9b}$, at each occurrence, is independently selected from $C_{1-6}$ alkyl substituted with 0-3 $R^{9e}$, $C_{2-8}$ alkenyl substituted with 0-3 $R^{9e}$, $C_{2-8}$ alkynyl substituted with 0-3 $R^{9e}$, a $(CH_2)_r$—$C_{3-6}$ carbocyclic residue substituted with 0-2 $R^{9e}$, and a $(CH_2)_r$-5-6 membered heterocyclic system containing 1-4 heteroatoms selected from N, O, and S, substituted with 0-3 $R^{9e}$;

$R^{9d}$, at each occurrence, is independently selected from H, methyl, —$CF_3$, $C_{2-6}$ alkyl substituted with 0-3 $R^{9e}$, $C_{3-6}$ alkenyl substituted with 0-3 $R^{9e}$, $C_{3-6}$ alkynyl substituted with 0-3 $R^{9e}$, a $C_{3-10}$ carbocyclic residue substituted with 0-3 $R^{9e}$, and a $(CH_2)_r$-5-6 membered heterocyclic system containing 1-4 heteroatoms selected from N, O, and S, substituted with 0-3 $R^{9e}$;

$R^{9e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{9f}R^{9f}$, and $(CH_2)_r$phenyl;

$R^{9f}$, at each occurrence, is independently selected from H, $C_{1-6}$ alkyl, and $C_{3-6}$ cycloalkyl;

$R^{10}$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{10d}$, $(CRR)_rS(O)_pR^{10d}$, $(CRR)_rC(O)R^{10b}$, $(CRR)_rNR^{10a}R^{10a}$, $(CRR)_rC(O)NR^{10a}R^{10a}$, $(CRR)_rC(O)NR^{10a}OR^{10d}$, $(CRR)_rSO_2NR^{10a}R^{10a}$, $(CRR)_rC(O)OR^{10d}$, a $(CRR)_r$—$C_{3-10}$ carbocyclic residue substituted with 0-5 $R^{10e}$, and a $(CRR)_r$-5-10 membered heterocyclic system containing 1-4 heteroatoms selected from N, O, and S, substituted with 0-3 $R^{10e}$;

alternatively, $R^{10}$ and $R^{11}$ join to form a $C_{3-6}$ cycloalkyl substituted with 0-2 $R^{10g}$, a 5-6 membered ring lactam substituted with 0-2 $R^{10g}$, or a 5-6 membered ring lactone substituted with 0-2 $R^{10g}$;

$R^{10a}$, at each occurrence, is independently selected from H, methyl, $C_{2-6}$ alkyl substituted with 0-3 $R^{10e}$, $C_{3-8}$ alkenyl substituted with 0-3 $R^{10e}$, $C_{3-8}$ alkynyl substituted with 0-3 $R^{10e}$, $(CH_2)_rC_{3-6}$ cycloalkyl, a $(CH_2)_r$—$C_{3-10}$ carbocyclic residue substituted with 0-5 $R^{10e}$, and a $(CH_2)_r$-5-10 membered heterocyclic system containing 1-4 heteroatoms selected from N, O, and S, substituted with 0-3 $R^{10e}$;

$R^{10b}$, at each occurrence, is independently selected from $C_{1-6}$ alkyl substituted with 0-3 $R^{10e}$, $C_{2-8}$ alkenyl substituted with 0-3 $R^{10e}$, $C_{2-8}$ alkynyl substituted with 0-3 $R^{10e}$, a $(CH_2)_r$—$C_{3-6}$ carbocyclic residue substituted with 0-2 $R^{10e}$, and a $(CH_2)_r$-5-6 membered heterocyclic system containing 1-4 heteroatoms selected from N, O, and S, substituted with 0-3 $R^{10e}$;

$R^{10d}$, at each occurrence, is independently selected from H, methyl, —$CF_3$, $C_{2-6}$ alkyl substituted with 0-3 $R^{10e}$, $C_{3-6}$ alkenyl substituted with 0-3 $R^{10e}$, $C_{3-6}$ alkynyl substituted with 0-3 $R^{10e}$, a $C_{3-10}$ carbocyclic residue substituted with 0-3 $R^{10e}$, and a $(CH_2)_r$-5-6 membered heterocyclic system containing 1-4 heteroatoms selected from N, O, and S, substituted with 0-3 $R^{10e}$;

$R^{10e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-16}$ alkyl, SH, $(CH_2)_rSC_{1-5}$ alkyl, $(CH_2)_rNR^{10f}R^{10f}$, and $(CH_2)_r$phenyl;

$R^{10f}$, at each occurrence, is independently selected from H, $C_{1-6}$ alkyl, and $C_{3-6}$ cycloalkyl;

$R^{10g}$ is selected from $(CHR)_qOH$, $(CHR)_qSH$, $(CHR)_qOR^{10d}$, $(CHR)_qS(O)_pR^{10d}$, $(CHR)_rC(O)R^{10b}$, $(CHR)_qNR^{10a}R^{10a}$, $(CHR)_rC(O)NR^{10a}R^{10a}$, $(CHR)_rC(O)NR^{10a}OR^{10d}$, $(CHR)_qSO_2NR^{10a}R^{10a}$, $(CHR)_rC(O)OR^{10d}$, and a $(CHR)_r$—$C_{3-10}$ carbocyclic residue substituted with 0-5 $R^{10e}$;

$R^{11}$, is selected from H, $C_{1-6}$ alkyl, $C_{2-6}$ alkenyl, $C_{2-6}$ alkynyl, $(CRR)_rOH$, $(CRR)_rSH$, $(CRR)_rOR^{11d}$, $(CRR)_rS(O)_pR^{11d}$, $(CRR)_rC(O)R^{11b}$, $(CRR)_rNR^{11a}R^{11a}$, $(CRR)_rC(O)NR^{11a}R^{11a}$, $(CRR)_rC(O)NR^{11a}OR^{11d}$, $(CRR)_rSO_2NR^{11a}R^{11a}$, $(CRR)_rC(O)OR^{11d}$, a $(CRR)_r$—$C_{3-10}$ carbocyclic residue substituted with 0-5 $R^{11e}$, and a $(CRR)_r$-5-10 membered heterocyclic system containing 1-4 heteroatoms selected from N, O, and S, substituted with 0-3 $R^{11e}$;

$R^{11a}$, at each occurrence, is independently selected from H, methyl, $C_{2-6}$ alkyl substituted with 0-3 $R^{11e}$, $C_{3-8}$ alkenyl substituted with 0-3 $R^{11e}$, $C_{3-8}$ alkynyl substituted with 0-3 $R^{11e}$, $(CH_2)_rC_{3-6}$ cycloalkyl, a $(CH_2)_r$—$C_{3-10}$ carbocyclic residue substituted with 0-5 $R^{11e}$, and a $(CH_2)_r$-5-10 membered heterocyclic system containing 1-4 heteroatoms selected from N, O, and S, substituted with 0-3 $R^{11e}$;

$R^{11b}$, at each occurrence, is independently selected from $C_{1-6}$ alkyl substituted with 0-3 $R^{11e}$, $C_{2-8}$ alkenyl substituted with 0-3 $R^{11e}$, $C_{2-8}$ alkynyl substituted with 0-3 $R^{11e}$, a $(CH_2)_r$—$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-6}$ alkyl substituted with 0-3 $R^{11e}$, $C_{3-6}$ alkenyl substituted with 0-3 $R^{11e}$, $C_{3-6}$ alkynyl substituted with 0-3 $R^{11e}$, a $C_{3-10}$ carbocyclic residue substituted with 0-3 $R^{11e}$, and a $(CH_2)_r$-5-6 membered heterocyclic system containing 1-4 heteroatoms selected from N, O, and S, substituted with 0-3 $R^{11e}$;

$R^{11e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-16}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is independently selected from H, $C_{1-6}$ alkyl, and $C_{3-6}$ cycloalkyl;

$R^{12}$ is selected from H, $C_{1-6}$ alkyl, $C_{2-6}$ alkenyl, $C_{2-6}$ alkynyl, $(CRR)_qOH$, $(CRR)_qSH$, $(CRR)_qOR^{12d}$, $(CRR)_qS(O)_pR^{12d}$, $(CRR)_rC(O)R^{12b}$, $(CRR)_rNR^{12a}R^{12a}$, $(CRR)_rC(O)NR^{12a}R^{12a}$, $(CRR)_rC(O)NR^{12a}OR^{12d}$, $(CRR)_qSO_2NR^{12a}R^{12a}$, $(CRR)_rC(O)OR^{12d}$, a $(CRR)_r$—$C_{3-10}$ carbocyclic residue substituted with 0-5 $R^{12e}$, and a $(CRR)_r$-5-10 membered heterocyclic system containing 1-4 heteroatoms selected from N, O, and S, substituted with 0-3 $R^{12e}$;

$R^{12a}$, at each occurrence, is independently selected from H, methyl, $C_{2-6}$ alkyl substituted with 0-3 $R^{12e}$, $C_{3-8}$ alkenyl substituted with 0-3 $R^{12e}$, $C_{3-8}$ alkynyl substituted with 0-3 $R^{12e}$, $(CH_2)_rC_{3-6}$ cycloalkyl, a $(CH_2)_r$—$C_{3-10}$ carbocyclic residue substituted with 0-5 $R^{12e}$, and a $(CH_2)_r$-5-10 membered heterocyclic system containing 1-4 heteroatoms selected from N, O, and S, substituted with 0-3 $R^{12e}$;

$R^{12b}$, at each occurrence, is independently selected from $C_{1-6}$ alkyl substituted with 0-3 $R^{12e}$, $C_{2-8}$ alkenyl substituted with 0-3 $R^{12e}$, $C_{2-8}$ alkynyl substituted with 0-3 $R^{12e}$, a $(CH_2)_r$—$C_{3-6}$ carbocyclic residue substituted with 0-2 $R^{12e}$, and a $(CH_2)_r$-5-6 membered heterocyclic system containing 1-4 heteroatoms selected from N, O, and S, substituted with 0-3 $R^{12e}$;

$R^{12d}$, at each occurrence, is independently selected from H, methyl, —$CF_3$, $C_{2-6}$ alkyl substituted with 0-3 $R^{12e}$, $C_{3-6}$ alkenyl substituted with 0-3 $R^{12e}$, $C_{3-6}$ alkynyl substituted with 0-3 $R^{12e}$, a $C_{3-10}$ carbocyclic residue substituted with 0-3 $R^{12e}$, and a $(CH_2)_r$-5-6 membered heterocyclic system containing 1-4 heteroatoms selected from N, O, and S, substituted with 0-3 $R^{12e}$;

$R^{12e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is independently selected from H, $C_{1-6}$ alkyl, and $C_{3-6}$ cycloalkyl;

$R^{13}$, at each occurrence, is independently selected from H, and $C_{1-4}$alkyl substituted with 0-1 $R^{13b}$, —OH, —$NH_2$, F, Cl, Br, I, —$OR^{13c}$, —$N(R^{13c})_2$, and $C_{1-4}$ alkyl substituted with 0-3 $R^{13b}$;

$R^{13b}$, at each occurrence, is independently selected from —OH, —SH, $NR^{13c}R^{13c}$, —$C(O)NR^{13c}R^{13c}$, and —$NHC(O)R^{13c}$;

$R^{13c}$ is selected from H, $C_{1-4}$ alkyl and $C_{3-6}$ cycloalkyl;

$R^{14}$ is independently selected from H, and $C_{1-4}$alkyl substituted with 0-1 $R^{14b}$;

$R^{14b}$, at each occurrence, is independently selected from —OH, —SH, $NR^{14c}R^{14c}$, —$C(O)NR^{14c}R^{14c}$, and —$NHC(O)R^{14c}$;

$R^{14c}$ is selected from H, $C_{1-4}$ alkyl and $C_{3-6}$ cycloalkyl;

$R^{17}$ is selected from H, $C_{1-4}$ alkyl, and $C_{3-4}$ cycloalkyl;

$R^{18}$ is selected from H, $C_{1-4}$ alkyl, and $C_{3-4}$ cycloalkyl;

$R^{19}$ is selected from H, $C_{1-4}$ alkyl, $C_{3-4}$ cycloalkyl, —C(O)H, and —C(O)—$C_{1-4}$alkyl;

$R^{24}$, at each occurrence, is independently selected from H and $C_{1-4}$alkyl;

alternatively, two $R^{24}$s, along with the carbon atom to which they are attached, join to form a $C_{3-6}$ carbocyclic ring;

$R^{25}$, at each occurrence, is independently selected from H, $C_{1-4}$alkyl, OH, $NH_2$, —O—$C_{1-4}$ alkyl, $NR^{25a}R^{25a}$, $C(O)NR^{25a}R^{25a}$, $NR^{25a}C(O)R^{25b}$, $NR^{25a}C(O)OR^{25d}$, $OC(O)NR^{25a}R^{25a}$, and $(CHR)_rC(O)OR^{25d}$;

alternatively, two $R^{25}$s, along with the carbon atom or atoms to which they are attached, join to form a $C_{3-6}$ carbocyclic ring;

$R^{25a}$, at each occurrence, is independently selected from H, and $C_{1-4}$ alkyl, $R^{25b}$, at each occurrence, is independently selected from H, $C_{1-4}$ alkyl, $C_{3-6}$ alkenyl, and $C_{3-6}$ alkynyl;

$R^{25d}$, at each occurrence, is independently selected from $C_{1-4}$ alkyl, $C_{3-6}$ alkenyl, and $C_{3-6}$ alkynyl;

$R^{26}$ is selected from $C_{1-4}$ alkyl;

n is selected from 0, 1, 2, and 3;

l is selected from 0 and 1;

m is selected from 0 and 1;

p, at each occurrence, is selected from 0, 1, or 2;

q, at each occurrence, is selected from 1, 2, 3, or 4;

r, at each occurrence, is selected from 0, 1, 2, 3, or 4;

s is selected from 0 and 1; and t is selected form 1, 2 and 3.

Thus, in another embodiment, the present invention provides novel compounds of formula (I):

$$R^1\underset{R^{17}}{N}-(CR^6R^7)-(CR^8R^9)_m-(CR^{10}R^{11})_l-(CR^{12}R^3)-N \begin{array}{c} Q \\ \diagup \\ \diagdown \end{array} Z-R^2 \quad (I)$$

(with substituents $R^{14}$, $(R^{13})_s$, a, b, n on the ring)

or a stereoisomer or a pharmaceutically acceptable salt thereof, wherein:

Z is selected from a bond, —$NR^{18}C(O)$—, —$NR^{18}C(S)$—, —$NR^{18}C(O)NH$—, —$NR^{18}C(S)NH$—, —$NR^{18}SO_2$—, —$NR^{18}SO_2NH$—, —$C(O)NR^{18}$—, —$OC(O)NR^{18}$—, —$NR^{18}C(O)O$—, —$(CR^{25}R^{25})_t$—, —$CR^{24}$=$CR^{24}$—, —$CR^{25}R^{25}C(O)$—, —$C(O)CR^{25}R^{25}$—, —$CR^{25}R^{25}C(=N—OR^{26})$—, —O—$CR^{24}R^{24}$—, —$CR^{24}R^{24}$—O—, —O—, —$NR^{19}$—, —$NR^{19}$—$CR^{24}R^{24}$—, —$CHR^{24}$—$NR^{19}$—, —$S(O)_p$—, —$S(O)_p$—$CR^{24}R^{24}$—, and —$S(O)_p$—$NR^{19}$—;

Q is selected from O or S;

wherein neither Z nor $R^{13}$ are connected to a carbon atom labeled (b);

bond (a) is a single or double bond;

alternatively, when n is equal to 2, two atoms labeled (b) may join through a double bond;

$R^1$ is selected from H, $C_{1-6}$ alkyl substituted with 0-3 $R^4$, $C_{2-6}$ alkenyl substituted with 0-3 $R^4$, $C_{2-6}$ alkynyl substituted with 0-3 $R^4$, $R^2$ is selected from a $C_{6-10}$ aryl group substituted with 0-5 $R^5$ and a 5-10 membered heteroaryl system containing 1-4 heteroatoms selected from N, O, and S, substituted with 0-3 $R^5$;

$R^3$ is selected from H, $(CRR)_qOH$, $(CRR)_qSH$, $(CRR)_qOR^{3d}$, $(CRR)_qS(O)_pR^{3d}$, $(CRR)_rC(O)R^{3b}$, $(CRR)_qNR^{3a}R^{3a}$, $(CRR)_rC(O)NR^{3a}R^{3a}$, $(CRR)_rC(O)NR^{3a}OR^{3d}$, $(CRR)_qSO_2NR^{3a}R^{3a}$, $(CRR)_rC(O)OR^{3d}$, a $(CRR)_r$—$C_{3-10}$ carbocyclic residue substituted with 0-5 $R^{3e}$, and a $(CRR)_r$-5-10 membered heterocyclic system containing 1-4 heteroatoms selected from N, O, and S, substituted with 0-3 $R^{3e}$;

with the proviso that $R^3$ is not H if $R^6$ is H;

alternatively, $R^3$ and $R^{12}$ join to form a $C_{3-6}$ cycloalkyl substituted with 0-2 $R^{3g}$, a 5-6 membered lactam ring in which carbon atoms of the ring are substituted with 0-2 $R^{3g}$, or a 5-6 membered lactone ring in which carbon atoms of the ring are substituted with 0-2 $R^{3g}$;

$R^{3a}$, at each occurrence, is independently selected from H, methyl substituted with 0-1 $R^{3c}$, $C_{2-6}$ alkyl substituted with 0-3 $R^{3e}$, $C_{3-8}$ alkenyl substituted with 0-3 $R^{3e}$, $C_{3-8}$ alkynyl substituted with 0-3 $R^{3e}$, $(CH_2)_rC_{3-6}$ cycloalkyl, a $(CH_2)_r$—$C_{3-10}$ carbocyclic residue substituted with 0-5 $R^{3e}$, and a $(CH_2)_r$-5-10 membered heterocyclic system containing 1-4 heteroatoms selected from N, O, and S, substituted with 0-3 $R^{3e}$;

$R^{3b}$, at each occurrence, is independently selected from $C_{1-6}$ alkyl substituted with 0-3 $R^{3e}$, $C_{2-8}$ alkenyl substituted with 0-3 $R^{3e}$, $C_{2-8}$ alkynyl substituted with 0-3 $R^{3e}$, a $(CH_2)_r$—$C_{3-6}$ carbocyclic residue substituted with 0-2 $R^{3e}$, and a $(CH_2)_r$-5-6 membered heterocyclic system containing 1-4 heteroatoms selected from N, O, and S, substituted with 0-3 $R^{3e}$;

$R^{3c}$ is independently selected from —$C(O)R^{3b}$, —$C(O)OR^{3d}$, —$C(O)NR^{3f}R^{3f}$, and $(CH_2)_r$phenyl;

$R^{3d}$, at each occurrence, is independently selected from H, methyl, —$CF_3$, $C_{2-6}$ alkyl substituted with 0-3 $R^{3e}$, $C_{3-6}$ alkenyl substituted with 0-3 $R^{3e}$, $C_{3-6}$ alkynyl substituted with 0-3 $R^{3e}$, a $C_{3-10}$ carbocyclic residue substituted with 0-3 $R^{3e}$, and a $(CH_2)_r$-5-6 membered heterocyclic system containing 1-4 heteroatoms selected from N, O, and S, substituted with 0-3 $R^{3e}$;

$R^{3e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{3f}R^{3f}$, and $(CH_2)_r$phenyl;

$R^{3f}$, at each occurrence, is selected from H, $C_{1-6}$ alkyl, and $C_{3-6}$ cycloalkyl;

$R^{3g}$ is selected from $(CHR)_rOH$, $(CHR)_rSH$, $(CHR)_rOR^{3d}$, $(CHR)_rS(O)_rR^{3d}$, $(CHR)_rC(O)R^{3b}$, $(CHR)_rNR^{3a}R^{3a}$, $(CHR)_rC(O)NR^{3a}R^{3a}$, $(CHR)_rC(O)NR^{3a}OR^{3d}$, $(CHR)_rSO_2NR^{3a}R^{3a}$, $(CHR)_rC(O)OR^{3d}$, and a $(CHR)_r$—$C_{3-10}$ carbocyclic residue substituted with 0-5 $R^{3e}$;

R, at each occurrence, is independently selected from H, $C_{1-6}$ alkyl, $C_{2-8}$ alkenyl, $C_{2-8}$ alkynyl, $(CH_2)_rC_{3-6}$ cycloalkyl, $(CH_2)_rC(O)NR^{3a}R^{3a}$, and $(CH_2)_rC(O)OR^{3d}$, $(CH_2)S(O)_2R^{3d}$, and $(CH_2)_r$phenyl substituted with 0-3 $R^{3e}$, and a $(CH_2)_r$-5-10 membered heterocyclic system containing 1-4 heteroatoms selected from N, O, and S, substituted with 0-3 $R^{3e}$;

$R^4$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_qNR^{4a}R^{4a}$, $(CR'R')_qOH$, $(CR'R')_qO(CR'R')_rR^{4d}$, $(CR'R')_qSH$, $(CR'R')_rC(O)H$, $(CR'R')_qS(CR'R')_rR^{4d}$, $(CR'R')_rC(O)OH$, $(CR'R')_rC(O)(CR'R')_rR^{4b}$, $(CR'R')_rC(O)NR^{4a}R^{4a}$, $(CR'R')_qNR^{4f}C(O)(CR'R')_rR^{4b}$, $(CR'R')_rC(O)O(CR'R')_rR^{4d}$, $(CR'R')_qOC(O)(CR'R')_rR^{4b}$, $(CR'R')_qNR^{4f}C(O)O(CR'R')_rR^{4d}$, $(CR'R')_qOC(O)NR^{4a}R^{4a}$, $(CR'R')_qNR^{4a}C(S)NR^{4a}(CR'R')_rR^{4d}$, $(CR'R')_qNR^{4a}C(O)NR^{4a}R^{4a}$, $(CR'R')_rC(=NR^{4f})NR^{4a}R^{4a}$, $(CR'R')_qNHC(=NR^{4f})NR^{4f}R^{4f}$, $(CR'R')_rS(O)_p(CR'R')_rR^{4b}$, $(CR'R')_rS(O)_2NR^{4a}R^{4a}$, $(CR'R')_qNR^{4a}S(O)_2NR^{4a}R^{4a}$, $(CR'R')_qNR^{4f}S(O)_2(CR'R')_rR^{4b}$, $C_{1-6}$ haloalkyl, $C_{2-8}$ alkenyl substituted with 0-3 R', $C_{2-8}$ alkynyl substituted with 0-3 R', and a $(CR'R')_r$nonaromatic-heterocycle containing 1-4 heteroatoms substituted with 0-3 $R^{4e}$;

alternatively, two $R^4$ on adjacent atoms on $R^1$ may join to form a cyclic acetal;

$R^{4a}$, at each occurrence, is independently selected from H, methyl substituted with 0-1$R^{4g}$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-10}$ cycloalkyl residue substituted with 0-5 $R^{4e}$, and a $(CH_2)_r$-5-10 membered nonaromatic heterocyclic system containing 1-4 heteroatoms selected from N, O, and S, substituted with 0-2 $R^{4e}$;

$R^{4b}$, at each occurrence, is selected from $C_{1-6}$ alkyl substituted with 0-2 $R^{4e}$, $C_{3-8}$ alkenyl substituted with 0-2 $R^{4e}$, $C_{3-8}$ alkynyl substituted with 0-2 $R^{4e}$, a $(CH_2)_rC_{3-6}$ cycloalkyl residue substituted with 0-3 $R^{4e}$, and a $(CH_2)_r$-5-6 membered nonaromatic heterocyclic system containing 1-4 heteroatoms selected from N, O, and S, substituted with 0-2 $R^{4e}$;

$R^{4d}$, at each occurrence, is selected from $C_{3-8}$ alkenyl substituted with 0-2 $R^{4e}$, $C_{3-8}$ alkynyl substituted with 0-2 $R^{4e}$, methyl, $CF_3$, $C_{2-6}$ alkyl substituted with 0-3 $R^{4e}$, a $(CH_2)_r$—$C_{3-10}$ cycloalkyl residue substituted with 0-3 $R^{4e}$, and a $(CH_2)_r$-5-6 membered nonaromatic heterocyclic system containing 1-4 heteroatoms selected from N, O, and S, substituted with 0-3 $R^{4e}$;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, and $(CH_2)_rNR^{4f}R^{4f}$;

$R^{4f}$, at each occurrence, is selected from H, $C_{1-5}$ alkyl, and $C_{3-6}$ cycloalkyl, and phenyl;

$R^{4g}$ is independently selected from —$C(O)R^{4b}$, —$C(O)OR^{4d}$, and —$C(O)NR^{4f}R^{4f}$;

$R^5$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{5a}R^{5a}$, $(CR'R')_rOH$, $(CR'R')_rO(CR'R')_rR^{5d}$, $(CR'R')_rSH$, $(CR'R')_rC(O)H$, $(CR'R')_rS(CR'R')_rR^{5d}$, $(CR'R')_rC(O)OH$, $(CR'R')_rC(O)(CR'R')_rR^{5b}$, $(CR'R')_rC(O)NR^{5a}R^{5a}$, $(CR'R')_rNR^{5f}C(O)(CR'R')_rR^{5b}$, $(CR'R')_rC(O)O(CR'R')_rR^{5d}$, $(CR'R')_rOC(O)(CR'R')_rR^{5b}$, $CR'R')_rNR^{5f}C(O)O(CR'R')_rR^{5d}$, $(CR'R')_rOC(O)NR^{5a}R^{5a}$, $(CR'R')_rNR^{5a}C(O)NR^{5a}R^{5a}$, $(CR'R')_rC(=NR^{5f})NR^{5a}R^{5a}$, $(CR'R')_rNHC(=NR^{5f})NR^{5f}R^{5f}$, $(CR'R')_rS(O)_p(CR'R')_rR^{5b}$, $(CR'R')_rS(O)_2NR^{5a}R^{5a}$, $(CR'R')_rNR^{5a}S(O)_2NR^{5a}R^{5a}$, $(CR'R')_rNR^{5f}S(O)_2(CR'R')_rR^{5b}$, $C_{1-6}$ haloalkyl, $C_{2-8}$ alkenyl substituted with 0-3 $R^1$, $C_{2-8}$ alkynyl substituted with 0-3 R', $(CR'R')_r$phenyl substituted with 0-3 $R^{5e}$, and a $(CR'R')_r$-5-10 membered heterocyclic system containing 1-4 heteroatoms selected from N, O, and S, substituted with 0-2 $R^{5c}$;

alternatively, two $R^5$ on adjacent atoms on $R^2$ may join to form a cyclic acetal;

$R^{5a}$, at each occurrence, is independently selected from H, methyl substituted with 0-1 $R^{5g}$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-10}$ carbocyclic residue substituted with 0-5 $R^{5e}$, and a $(CH_2)_r$-5-10 membered heterocyclic system containing 1-4 heteroatoms selected from N, O, and S, substituted with 0-2 $R^{5e}$;

$R^{5b}$, at each occurrence, is independently selected from $C_{1-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, a $(CH_2)_rC_{3-6}$ carbocyclic residue substituted with 0-3 $R^{5e}$, and a $(CH_2)_r$-5-6 membered heterocyclic system containing 1-4 heteroatoms selected from N, O, and S, substituted with 0-2 $R^{5e}$;

$R^{5d}$, at each occurrence, is independently selected from $C_{3-8}$ alkenyl substituted with 0-2 $R^{5e}$, $C_{3-8}$ alkynyl substituted with 0-2 $R^{5e}$, methyl, $CF_3$, $C_{2-6}$ alkyl substituted with 0-3 $R^{5e}$, a $(CH_2)_r$—$C_{3-10}$ carbocyclic residue substituted with 0-3 $R^{5e}$, and a $(CH_2)_r$-5-6 membered heterocyclic system containing 1-4 heteroatoms selected from N, O, and S, substituted with 0-3 $R^{5e}$;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-5}$ alkyl, and $C_{3-6}$ cycloalkyl, and phenyl;

$R^{5g}$ is independently selected from —$C(O)R^{5b}$, —$C(O)OR^{5d}$, —$C(O)NR^{5f}R^{5f}$, and $(CH_2)_r$phenyl;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{5e}$;

R', is selected from H, $C_{1-6}$ alkyl, $C_{2-6}$ alkenyl, $C_{2-6}$ alkynyl, $(CRR)_qOH$, $(CRR)_qSH$, $(CRR)_qOR^{6d}$, $(CRR)_qS(O)_pR^{6d}$, $(CRR)_rC(O)R^{6b}$, $(CRR)_rNR^{6a}R^{6a}$, $(CRR)_rC(O)NR^{6a}R^{6a}$, $(CRR)_rC(O)NR^{6a}OR^{6d}$, $(CRR)SO_2NR^{6a}R^{6a}$, $(CRR)_rC(O)OR^{6d}$, a $(CRR)_r$—$C_{3-10}$ carbocyclic residue substituted with 0-5 $R^{6e}$, and a $(CRR)_r$-5-10 membered heterocyclic system containing 1-4 heteroatoms selected from N, O, and S, substituted with 0-3 $R^{6e}$;

alternatively, $R^6$ and $R^7$ join to form a $C_{3-6}$ cycloalkyl substituted with 0-2 $R^{6g}$, a 5-6 membered ring lactam substituted with 0-2 $R^{6g}$, or a 5-6 membered ring lactone substituted with 0-2 $R^{6g}$;

$R^{6a}$, at each occurrence, is independently selected from H, methyl, $C_{2-6}$ alkyl substituted with 0-3 $R^{6e}$, $C_{3-8}$ alkenyl substituted with 0-3 $R^{6e}$, $C_{3-8}$ alkynyl substituted with 0-3 $R^{6e}$, $(CH_2)_rC_{3-6}$ cycloalkyl, a $(CH_2)_r$—$C_{3-10}$ carbocyclic residue substituted with 0-5 $R^{6e}$, and a $(CH_2)_r$-5-10 membered heterocyclic system containing 1-4 heteroatoms selected from N, O, and S, substituted with 0-3 $R^{6e}$;

$R^{6b}$, at each occurrence, is independently selected from $C_{1-6}$ alkyl substituted with 0-3 $R^{6e}$, $C_{2-8}$ alkenyl substituted with 0-3 $R^{6e}$, $C_{2-8}$ alkynyl substituted with 0-3 $R^{6e}$, a $(CH_2)_r$—$C_{3-6}$ carbocyclic residue substituted with 0-2 $R^{6e}$, and a $(CH_2)_r$-5-6 membered heterocyclic system containing 1-4 heteroatoms selected from N, O, and S, substituted with 0-3 $R^{6e}$;

$R^{6d}$, at each occurrence, is independently selected from H, methyl, —$CF_3$, $C_{2-6}$ alkyl substituted with 0-3 $R^{6e}$, $C_{3-6}$ alkenyl substituted with 0-3 $R^{6e}$, $C_{3-6}$ alkynyl substituted with 0-3 $R^{6e}$, a $C_{3-10}$ carbocyclic residue substituted with 0-3 $R^{6e}$, and a $(CH_2)_r$-5-6 membered heterocyclic system containing 1-4 heteroatoms selected from N, O, and S, substituted with 0-3 $R^{6e}$;

$R^{6e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-16}$ alkyl, SH, $(CH_2)_rSC_{1-5}$ alkyl, $(CH_2)_rNR^{6f}R^{6f}$, and $(CH_2)_r$phenyl;

$R^{6f}$, at each occurrence, is independently selected from H, $C_{1-6}$ alkyl, and $C_{3-6}$ cycloalkyl;

$R^{6g}$ is selected from $(CHR)_qOH$, $(CHR)_qSH$, $(CHR)_qOR^{6d}$, $(CHR)_qS(O)_pR^{6d}$, $(CHR)_rC(O)R^{6b}$, $(CHR)_qNR^{6a}R^{6a}$, $(CHR)_rC(O)NR^{6a}R^{6a}$, $(CHR)_rC(O)NR^{6a}OR^{6d}$, $(CHR)_qSO_2NR^{6a}R^{6a}$, $(CHR)_rC(O)OR^{6d}$, and a (CHR) r-$C_{3-10}$ carbocyclic residue substituted with 0-5 $R^{6e}$;

$R^7$, is selected from H, $C_{1-6}$ alkyl, $C_{2-6}$ alkenyl, $C_{2-6}$ alkynyl, $(CRR)_qOH$, $(CRR)_qSH$, $(CRR)_qOR^{7d}$, $(CRR)_qS(O)_pR^{7d}$, $(CRR)_rC(O)R^{7b}$, $(CRR)_rNR^{7a}R^{7a}$, $(CRR)_rC(O)NR^{7a}R^{7a}$, $(CRR)_rC(O)NR^{7a}OR^{7d}$, $(CRR)_qSO_2NR^{7a}R^{7a}$, $(CRR)_rC$(O)$OR^{7d}$, a $(CRR)_r$—$C_{3-10}$ carbocyclic residue substituted with 0-5 $R^{7e}$, and a $(CRR)_r$-5-10 membered heterocyclic system containing 1-4 heteroatoms selected from N, O, and S, substituted with 0-3 $R^{7e}$;

$R^{7a}$, at each occurrence, is independently selected from H, methyl, $C_{2-6}$ alkyl substituted with 0-3 $R^{7e}$, $C_{3-8}$ alkenyl substituted with 0-3 $R^{7e}$, $C_{3-8}$ alkynyl substituted with 0-3 $R^{7e}$, $(CH_2)_rC_{3-6}$ cycloalkyl, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-3 $R^{7e}$;

$R^{7b}$, at each occurrence, is independently selected from $C_{1-6}$ alkyl substituted with 0-3 $R^{7e}$, $C_{2-8}$ alkenyl substituted with 0-3 $R^{7e}$, $C_{2-8}$ alkynyl substituted with 0-3 $R^{7e}$, a $(CH_2)_r$—$C_{3-6}$ carbocyclic residue substituted with 0-2 $R^{7e}$, and a $(CH_2)_r$-5-6 membered heterocyclic system containing 1-4 heteroatoms selected from N, O, and S, substituted with 0-3 $R^{7e}$;

$R^{7d}$, at each occurrence, is independently selected from H, methyl, —$CF_3$, $C_{2-6}$ alkyl substituted with 0-3 $R^{7e}$, $C_{3-6}$ alkenyl substituted with 0-3 $R^{7e}$, $C_{3-6}$ alkynyl substituted with 0-3 $R^{7e}$, a $C_{3-10}$ carbocyclic residue substituted with 0-3 $R^{7e}$, and a $(CH_2)_r$-5-6 membered heterocyclic system containing 1-4 heteroatoms selected from N, O, and S, substituted with 0-3 $R^{7e}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{7f}R^{7f}$, and $(CH_2)_r$phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{8d}$, $(CRR)_rS(O)_pR^{8d}$, $(CRR)_rC(O)R^{8b}$, $(CRR)_rNR^{8a}R^{8a}$, $(CRR)_rC(O)NR^{8a}R^{8a}$, $(CRR)_rC(O)NR^{8a}OR^{8d}$, $(CRR)_rSO_2NR^{8a}R^{8a}$, $(CRR)_rC(O)OR^{8d}$, a $(CRR)_r$—$C_{3-10}$ carbocyclic residue substituted with 0-5 $R^{8e}$, and a $(CRR)_r$-5-10 membered heterocyclic system containing 1-4 heteroatoms selected from N, O, and S, substituted with 0-3 $R^{8e}$;

alternatively, $R^8$ and $R^9$ join to form a $C_{3-6}$ cycloalkyl substituted with 0-2 $R^{8g}$, a 5-6 membered ring lactam substituted with 0-2 $R^{8g}$, or a 5-6 membered ring lactone substituted with 0-2 $R^{8g}$;

$R^{8a}$, at each occurrence, is independently selected from H, methyl, $C_{2-6}$ alkyl substituted with 0-3 $R^{8e}$, $C_{3-8}$ alkenyl substituted with 0-3 $R^{8e}$, $C_{3-8}$ alkynyl substituted with 0-3 $R^{8e}$, $(CH_2)_rC_{3-6}$ cycloalkyl, a $(CH_2)_r$—$C_{3-10}$ carbocyclic residue substituted with 0-5 $R^{8e}$, and a $(CH_2)_r$-5-10 membered heterocyclic system containing 1-4 heteroatoms selected from N, O, and S, substituted with 0-3 $R^{8e}$;

$R^{8b}$, at each occurrence, is independently selected from $C_{1-6}$ alkyl substituted with 0-3 $R^{8e}$, $C_{2-8}$ alkenyl substituted with 0-3 $R^{8e}$, $C_{2-8}$ alkynyl substituted with 0-3 $R^{8e}$, a $(CH_2)_r$—$C_{3-6}$ carbocyclic residue substituted with 0-2 $R^{8e}$, and a $(CH_2)_r$-5-6 membered heterocyclic system containing 1-4 heteroatoms selected from N, O, and S, substituted with 0-3 $R^{8e}$;

$R^{8d}$, at each occurrence, is independently selected from H, methyl, —$CF_3$, $C_{2-6}$ alkyl substituted with 0-3 $R^{8e}$, $C_{3-6}$ alkenyl substituted with 0-3 $R^{8e}$, $C_{3-6}$ alkynyl substituted with 0-3 $R^{8e}$, a $C_{3-10}$ carbocyclic residue substituted with 0-3 $R^{8e}$, and a $(CH_2)_r$-5-6 membered heterocyclic system containing 1-4 heteroatoms selected from N, O, and S, substituted with 0-3 $R^{8e}$;

$R^{8e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-16}$ alkyl, SH, (CH$_2$)$_r$SC$_{1-5}$ alkyl, (CH$_2$)$_r$NR$^{8f}$R$^{8f}$, and (CH$_2$)$_r$phenyl;

R$^{8f}$, at each occurrence, is independently selected from H, C$_{1-6}$ alkyl, and C$_{3-6}$ cycloalkyl;

R$^{8g}$ is selected from (CHR)$_q$OH, (CHR)$_q$SH, (CHR)$_q$OR$^{8d}$, (CHR)$_q$S(O)$_p$R$^{8d}$, (CHR)$_r$C(O)R$^{8b}$, (CHR)$_q$NR$^{8a}$R$^{8a}$, (CHR)$_r$C(O)NR$^{8a}$R$^{8a}$, (CHR)$_r$C(O)NR$^{8a}$OR$^{8d}$, (CHR)$_q$SO$_2$NR$^{8a}$R$^{8a}$, (CHR)$_r$C(O)OR$^{8d}$, and a (CHR)$_r$—C$_{3-10}$ carbocyclic residue substituted with 0-5 R$^{8e}$;

R$^9$ is selected from H, C$_{1-6}$ alkyl, C$_{2-6}$ alkenyl, C$_{2-6}$ alkynyl, (CRR)$_r$OH, (CRR)$_r$SH, (CRR)$_r$OR$^{9d}$, (CRR)$_r$S(O)$_p$R$^{9d}$, (CRR)$_r$C(O)R$^{9b}$, (CRR)$_r$NR$^{9a}$R$^{9a}$, (CRR)$_r$C(O)NR$^{9a}$R$^{9a}$, (CRR)$_r$C(O)NR$^{9a}$OR$^{9d}$, (CRR)$_r$SO$_2$NR$^{9a}$R$^{9a}$, (CRR)$_r$C(O)OR$^{9d}$, a (CRR)$_r$—C$_{3-10}$ carbocyclic residue substituted with 0-5 R$^{9e}$, and a (CRR)$_r$-5-10 membered heterocyclic system containing 1-4 heteroatoms selected from N, O, and S, substituted with 0-3 R$^{9e}$;

R$^{9a}$, at each occurrence, is independently selected from H, methyl, C$_{2-6}$ alkyl substituted with 0-3 R$^{9e}$, C$_{3-8}$ alkenyl substituted with 0-3 R$^{9e}$, C$_{3-8}$ alkynyl substituted with 0-3 R$^{9e}$, (CH$_2$)$_r$C$_{3-6}$ cycloalkyl, a (CH$_2$)$_r$—C$_{3-10}$ carbocyclic residue substituted with 0-5 R$^{9e}$, and a (CH$_2$)$_r$-5-10 membered heterocyclic system containing 1-4 heteroatoms selected from N, O, and S, substituted with 0-3 R$^{9e}$;

R$^{9b}$, at each occurrence, is independently selected from C$_{1-6}$ alkyl substituted with 0-3 R$^{9e}$, C$_{2-8}$ alkenyl substituted with 0-3 R$^{9e}$, C$_{2-8}$ alkynyl substituted with 0-3 R$^{9e}$, a (CH$_2$)$_r$—C$_{3-6}$ carbocyclic residue substituted with 0-2 R$^{9e}$, and a (CH$_2$)$_r$-5-6 membered heterocyclic system containing 1-4 heteroatoms selected from N, O, and S, substituted with 0-3 R$^{9e}$;

R$^{9d}$, at each occurrence, is independently selected from H, methyl, —CF$_3$, C$_{2-6}$ alkyl substituted with 0-3 R$^{9e}$, C$_{3-6}$ alkenyl substituted with 0-3 R$^{9e}$, C$_{3-6}$ alkynyl substituted with 0-3 R$^{9e}$, a C$_{3-10}$ carbocyclic residue substituted with 0-3 R$^{9e}$, and a (CH$_2$)$_r$-5-6 membered heterocyclic system containing 1-4 heteroatoms selected from N, O, and S, substituted with 0-3 R$^{9e}$;

R$^{9e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{9f}$R$^{9f}$, and (CH$_2$)$_r$phenyl;

R$^{9f}$, at each occurrence, is independently selected from H, C$_{1-6}$ alkyl, and C$_{3-6}$ cycloalkyl;

R$^{10}$ is selected from H, C$_{1-6}$ alkyl, C$_{2-6}$ alkenyl, C$_{2-6}$ alkynyl, (CRR)$_r$OH, (CRR)$_r$SH, (CRR)$_r$OR$^{10d}$, (CRR)$_r$S(O)$_p$R$^{10d}$, (CRR)$_r$C(O)R$^{10b}$, (CRR)$_r$NR$^{10a}$R$^{10a}$, (CRR)$_r$C(O)NR$^{10a}$R$^{10a}$, (CRR)$_r$C(O)NR$^{10a}$OR$^{10d}$, (CRR)$_r$SO$_2$NR$^{10a}$R$^{10a}$, (CRR)$_r$C(O)OR$^{10d}$, a (CRR)$_r$—C$_{3-10}$ carbocyclic residue substituted with 0-5 R$^{10e}$, and a (CRR)$_r$-5-10 membered heterocyclic system containing 1-4 heteroatoms selected from N, O, and S, substituted with 0-3 R$^{10e}$;

alternatively, R$^{10}$ and R$^{11}$ join to form a C$_{3-6}$ cycloalkyl substituted with 0-2 R$^{10g}$, a 5-6 membered ring lactam substituted with 0-2 R$^{10g}$, or a 5-6 membered ring lactone substituted with 0-2 R$^{10g}$;

R$^{10a}$, at each occurrence, is independently selected from H, methyl, C$_{2-6}$ alkyl substituted with 0-3 R$^{10e}$, C$_{3-8}$ alkenyl substituted with 0-3 R$^{10e}$, C$_{3-8}$ alkynyl substituted with 0-3 R$^{10e}$, (CH$_2$)$_r$C$_{3-6}$ cycloalkyl, a (CH$_2$)$_r$—C$_{3-10}$ carbocyclic residue substituted with 0-5 R$^{10e}$, and a (CH$_2$)$_r$-5-10 membered heterocyclic system containing 1-4 heteroatoms selected from N, O, and S, substituted with 0-3 R$^{10e}$;

R$^{10b}$, at each occurrence, is independently selected from C$_{1-6}$ alkyl substituted with 0-3 R$^{10e}$, C$_{2-8}$ alkenyl substituted with 0-3 R$^{10e}$, C$_{2-8}$ alkynyl substituted with 0-3 R$^{10e}$, a (CH$_2$)$_r$—C$_{3-6}$ carbocyclic residue substituted with 0-2 R$^{10e}$, and a (CH$_2$)$_r$-5-6 membered heterocyclic system containing 1-4 heteroatoms selected from N, O, and S, substituted with 0-3 R$^{10e}$;

R$^{10d}$, at each occurrence, is independently selected from H, methyl, —CF$_3$, C$_{2-6}$ alkyl substituted with 0-3 R$^{10e}$, C$_{3-6}$ alkenyl substituted with 0-3 R$^{10e}$, C$_{3-6}$ alkynyl substituted with 0-3 R$^{10e}$, a C$_{3-10}$ carbocyclic residue substituted with 0-3 R$^{10e}$, and a (CH$_2$)$_r$-5-6 membered heterocyclic system containing 1-4 heteroatoms selected from N, O, and S, substituted with 0-3 R$^{10e}$;

R$^{10e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-16}$ alkyl, SH, (CH$_2$)$_r$SC$_{1-5}$ alkyl, (CH$_2$)$_r$NR$^{10f}$R$^{10f}$, and (CH$_2$)$_r$phenyl;

R$^{10f}$, at each occurrence, is independently selected from H, C$_{1-6}$ alkyl, and C$_{3-6}$ cycloalkyl;

R$^{10g}$ is selected from (CHR)$_q$OH, (CHR)$_q$SH, (CHR)$_q$OR$^{10d}$, (CHR)$_q$S(O)$_p$R$^{10d}$, (CHR)$_r$C(O)R$^{10b}$, (CHR)$_q$NR$^{10a}$R$^{10a}$, (CHR)$_r$C(O)NR$^{10a}$R$^{10a}$, (CHR)$_r$C(O)NR$^{10a}$OR$^{10d}$, (CHR)$_q$SO$_2$NR$^{10a}$R$^{10a}$, (CHR)$_r$C(O)OR$^{10d}$, and a (CHR)$_r$—C$_{3-10}$ carbocyclic residue substituted with 0-5 R$^{10e}$;

R$^{11}$, is selected from H, C$_{1-6}$ alkyl, C$_{2-6}$ alkenyl, C$_{2-6}$ alkynyl, (CRR)$_r$OH, (CRR)$_r$SH, (CRR)$_r$OR$^{11d}$, (CRR)$_r$S(O)$_p$R$^{11d}$, (CRR)$_r$C(O)R$^{11b}$, (CRR)$_r$NR$^{11a}$R$^{11a}$, (CRR)$_r$C(O)NR$^{11a}$R$^{11a}$, (CRR)$_r$C(O)NR$^{11a}$OR$^{11d}$, (CRR)$_r$SO$_2$NR$^{11a}$R$^{11a}$, (CRR)$_r$C(O)OR$^{11d}$, a (CRR)$_r$—C$_{3-10}$ carbocyclic residue substituted with 0-5 R$^{11e}$, and a (CRR)$_r$-5-10 membered heterocyclic system containing 1-4 heteroatoms selected from N, O, and S, substituted with 0-3 R$^{11e}$;

R$^{11a}$, at each occurrence, is independently selected from H, methyl, C$_{2-6}$ alkyl substituted with 0-3 R$^{11e}$, C$_{3-8}$ alkenyl substituted with 0-3 R$^{11e}$, C$_{3-8}$ alkynyl substituted with 0-3 R$^{11e}$, (CH$_2$)$_r$C$_{3-6}$ cycloalkyl, a (CH$_2$)$_r$—C$_{3-10}$ carbocyclic residue substituted with 0-5 R$^{11e}$, and a (CH$_2$)$_r$-5-10 membered heterocyclic system containing 1-4 heteroatoms selected from N, O, and S, substituted with 0-3 R$^{11e}$;

R$^{11b}$, at each occurrence, is independently selected from C$_{1-6}$ alkyl substituted with 0-3 R$^{11e}$, C$_{2-8}$ alkenyl substituted with 0-3 R$^{11e}$, C$_{2-8}$ alkynyl substituted with 0-3 R$^{11e}$, a (CH$_2$)$_r$—C$_{3-6}$ carbocyclic residue substituted with 0-2 R$^{11e}$, and a (CH$_2$)$_r$-5-6 membered heterocyclic system containing 1-4 heteroatoms selected from N, O, and S, substituted with 0-3 R$^{11e}$;

R$^{11d}$, at each occurrence, is independently selected from H, methyl, —CF$_3$, C$_{2-6}$ alkyl substituted with 0-3 R$^{11e}$, C$_{3-6}$ alkenyl substituted with 0-3 R$^{11e}$, C$_{3-6}$ alkynyl substituted with 0-3 R$^{11e}$, a C$_{3-10}$ carbocyclic residue substituted with 0-3 R$^{11e}$, and a (CH$_2$)$_r$-5-6 membered heterocyclic system containing 1-4 heteroatoms selected from N, O, and S, substituted with 0-3 R$^{11e}$;

R$^{11e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-16}$ alkyl, SH, (CH$_2$)$_r$SC$_{1-5}$ alkyl, (CH$_2$)$_r$NR$^{11f}$R$^{11f}$, and (CH$_2$)$_r$phenyl;

R$^{11f}$, at each occurrence, is independently selected from H, C$_{1-6}$ alkyl, and C$_{3-6}$ cycloalkyl;

R$^{12}$ is selected from H, C$_{1-6}$ alkyl, C$_{2-6}$ alkenyl, C$_{2-6}$ alkynyl, (CRR)$_q$OH, (CRR)$_q$SH, (CRR)$_q$OR$^{12d}$, (CRR)$_q$S(O)$_p$R$^{12d}$, (CRR)$_r$C(O)R$^{12b}$, (CRR)$_r$NR$^{12a}$R$^{12a}$, (CRR)$_r$C (O)NR$^{12a}$R$^{12a}$, (CRR)$_r$C(O)NR$^{12a}$OR$^{12d}$, (CRR)$_q$SO$_2$NR$^{12a}$R$^{12a}$, (CRR)$_r$C(O)OR$^{12d}$, a (CRR)$_r$—C$_{3\text{-}10}$ carbocyclic residue substituted with 0-5 R$^{12e}$, and a (CRR)$_r$-5-10 membered heterocyclic system containing 1-4 heteroatoms selected from N, O, and S, substituted with 0-3 R$^{12e}$;

R$^{12a}$, at each occurrence, is independently selected from H, methyl, C$_{2\text{-}6}$ alkyl substituted with 0-3 R$^{12e}$, C$_{3\text{-}8}$ alkenyl substituted with 0-3 R$^{12e}$, C$_{3\text{-}8}$ alkynyl substituted with 0-3 R$^{12e}$, (CH$_2$)$_r$C$_{3\text{-}6}$ cycloalkyl, a (CH$_2$)$_r$—C$_{3\text{-}10}$ carbocyclic residue substituted with 0-5 R$^{12e}$, and a (CH$_2$)$_r$-5-10 membered heterocyclic system containing 1-4 heteroatoms selected from N, O, and S, substituted with 0-3 R$^{12e}$;

R$^{12b}$, at each occurrence, is independently selected from C$_{1\text{-}6}$ alkyl substituted with 0-3 R$^{12e}$, C$_{2\text{-}8}$ alkenyl substituted with 0-3 R$^{12e}$, C$_{2\text{-}8}$ alkynyl substituted with 0-3 R$^{12e}$, a (CH$_2$)$_r$—C$_{3\text{-}6}$ carbocyclic residue substituted with 0-2 R$^{12e}$, and a (CH$_2$)$_r$-5-6 membered heterocyclic system containing 1-4 heteroatoms selected from N, O, and S, substituted with 0-3 R$^{12e}$;

R$^{12d}$, at each occurrence, is independently selected from H, methyl, —CF$_3$, C$_{2\text{-}6}$ alkyl substituted with 0-3 R$^{12e}$, C$_{3\text{-}6}$ alkenyl substituted with 0-3 R$^{12e}$, C$_{3\text{-}6}$ alkynyl substituted with 0-3 R$^{12e}$, a C$_{3\text{-}10}$ carbocyclic residue substituted with 0-3 R$^{12e}$, and a (CH$_2$)$_r$-5-6 membered heterocyclic system containing 1-4 heteroatoms selected from N, O, and S, substituted with 0-3 R$^{12e}$;

R$^{12e}$, at each occurrence, is independently selected from C$_{1\text{-}6}$ alkyl, C$_{2\text{-}8}$ alkenyl, C$_{2\text{-}8}$ alkynyl, C$_{3\text{-}6}$ cycloalkyl, Cl, F, Br, I, CN, NO$_2$, (CF$_2$)$_r$CF$_3$, (CH$_2$)$_r$OC$_{1\text{-}5}$ alkyl, OH, —O—C$_{1\text{-}6}$ alkyl, SH, (CH$_2$)$_r$SC$_{1\text{-}5}$ alkyl, (CH$_2$)$_r$NR$^{12f}$R$^{12f}$, and (CH$_2$)$_r$phenyl;

R$^{12f}$, at each occurrence, is selected from H, C$_{1\text{-}6}$ alkyl, and C$_{3\text{-}6}$ cycloalkyl;

R$^{13}$, at each occurrence, is independently selected from H, and C$_{1\text{-}4}$alkyl substituted with 0-1 R$^{13b}$, —OH, —NH$_2$, F, Cl, Br, I, —OR$^{13c}$, —N(R$^{13c}$)$_2$, and C$_{1\text{-}4}$ alkyl substituted with 0-3 R$^{13b}$;

R$^{13b}$, at each occurrence, is independently selected from —OH, —SH, NR$^{13c}$R$^{13c}$, —C(O)NR$^{13c}$R$^{13c}$, and —NHC(O)R$^{13c}$;

R$^{13c}$ is selected from H, C$_{1\text{-}4}$ alkyl and C$_{3\text{-}6}$ cycloalkyl;

R$^{14}$ is independently selected from H, and C$_{1\text{-}4}$alkyl substituted with 0-1 R$^{14b}$;

R$^{14b}$, at each occurrence, is independently selected from —OH, —SH, NR$^{14c}$R$^{14c}$, —C(O)NR$^{14c}$R$^{14c}$, and —NHC(O)R$^{14c}$;

R$^{14c}$ is selected from H, C$_{1\text{-}4}$ alkyl and C$_{3\text{-}6}$ cycloalkyl;

R$^{17}$ is selected from H, C$_{1\text{-}4}$ alkyl, and C$_{3\text{-}4}$ cycloalkyl;

R$^{18}$ is selected from H, C$_{1\text{-}4}$ alkyl, and C$_{3\text{-}4}$ cycloalkyl;

R$^{19}$ is selected from H, C$_{1\text{-}4}$ alkyl, C$_{3\text{-}4}$ cycloalkyl, —C(O)H, and —C(O)—C$_{1\text{-}4}$alkyl;

R$^{24}$, at each occurrence, is independently selected from H and C$_{1\text{-}4}$alkyl;

alternatively, two R$^{24}$s, along with the carbon atom to which they are attached, join to form a C$_{3\text{-}6}$ carbocyclic ring;

R$^{25}$, at each occurrence, is independently selected from H, C$_{1\text{-}4}$alkyl, OH, NH$_2$, —O—C$_{1\text{-}4}$ alkyl, NR$^{25a}$R$^{25a}$, C(O)NR$^{25a}$R$^{25a}$, NR$^{25a}$C(O)R$^{25b}$, NR$^{25a}$C(O)OR$^{25d}$, OC(O)NR$^{25a}$R$^{25a}$, and (CHR)$_r$C(O)OR$^{25d}$;

alternatively, two R$^{25}$s, along with the carbon atom or atoms to which they are attached, join to form a C$_{3\text{-}6}$ carbocyclic ring;

R$^{25a}$, at each occurrence, is independently selected from H, and C$_{1\text{-}4}$ alkyl, R$^{25b}$, at each occurrence, is independently selected from H, C$_{1\text{-}4}$ alkyl, C$_{3\text{-}6}$ alkenyl, and C$_{3\text{-}6}$ alkynyl;

R$^{25d}$, at each occurrence, is independently selected from C$_{1\text{-}4}$ alkyl, C$_{3\text{-}6}$ alkenyl, and C$_{3\text{-}6}$ alkynyl;

R$^{26}$ is selected from C$_{1\text{-}4}$ alkyl;

n is selected from 0, 1, 2, and 3;

l is selected from 0 and 1;

m is selected from 0 and 1;

p, at each occurrence, is selected from 0, 1, or 2;

q, at each occurrence, is selected from 1, 2, 3, or 4;

r, at each occurrence, is selected from 0, 1, 2, 3, or 4;

s is selected from 0 and 1; and t is selected form 1, 2 and 3.

In another embodiment, the present invention provides novel compounds of formula (I), wherein R$^{17}$ is selected from H, methyl, ethyl, propyl, and i-propyl.

In another embodiment, the present invention provides novel compounds of formula (I), wherein R$^9$ and R$^{11}$ are H; and R$^8$ and R$^{10}$ are independently selected from H, methyl, ethyl, propyl, i-propyl, butyl, and cyclopropyl.

In another embodiment, the present invention provides novel compounds of formula (I), wherein R$^3$ is selected from (CRR)$_q$OH, (CRR)$_q$SH, (CRR)$_q$OR$^{3d}$, (CRR)$_q$S(O)$_p$R$^{3d}$, (CRR)$_r$C(O)R$^{3b}$, (CRR)$_q$NR$^{3a}$R$^{3a}$, (CRR)$_r$C(O)NR$^{3a}$R$^{3a}$, (CRR)$_r$C(O)NR$^{3a}$OR$^{3d}$, (CRR)$_q$SO$_2$NR$^{3a}$R$^{3a}$, (CRR)$_r$C(O)OR$^{3d}$, a (CRR)$_r$—C$_{3\text{-}10}$ carbocyclic residue substituted with 0-5 R$^{3e}$, and a (CRR)$_r$-5-10 membered heterocyclic system containing 1-4 heteroatoms selected from N, O, and S, substituted with 0-3 R$^{3e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, pyrrolidinyl, tetrahydrofuranyl, tetrahydrothiophenyl, 1,2,4-triazolyl, 1,2,3-triazolyl, tetrazolyl, thiadiazolyl, thiazolyl, oxazolyl, pyrazinyl, and pyrimidinyl;

R$^6$ is selected from H, C$_{1\text{-}6}$ alkyl, (CRR)$_q$OH, (CRR)$_q$SH, (CRR)$_q$OR$^{6d}$, (CRR)$_q$S(O)$_p$R$^{6d}$, (CRR)$_r$C(O)R$^{6b}$, (CRR)$_q$NR$^{6a}$R$^{6a}$, (CRR)$_r$C(O)NR$^{6a}$R$^{6a}$, (CRR)$_r$C(O)NR$^{6a}$OR$^{6d}$, (CRR)$_q$SO$_2$NR$^{6a}$R$^{6a}$, (CRR)$_r$C(O)OR$^{6d}$, a (CRR)$_r$—C$_{6\text{-}10}$ carbocyclic residue substituted with 0-5 R$^{6e}$, and a (CRR)$_r$-5-10 membered heterocyclic system containing 1-4 heteroatoms selected from N, O, and S, substituted with 0-6 R$^{6e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, pyrrolidinyl, tetrahydrofuranyl, tetrahydrothiophenyl, 1,2,4-triazolyl, 1,2,6-triazolyl, tetrazolyl, thiadiazolyl, thiazolyl, oxazolyl, pyrazinyl, and pyrimidinyl;

R$^7$ and R$^{12}$ are H;

alternatively, R$^3$ and R$^{12}$ join to form a C$_{3\text{-}6}$ cycloalkyl substituted with 0-2 R$^{3g}$, a 5-6 membered lactam ring substituted with 0-2 R$^{3g}$, or a 5-6 membered lactone ring substituted with 0-2 R$^{3g}$; and m+l is equal to 1.

In another embodiment, the present invention provides novel compounds of formula (I), wherein R$^1$ is selected from H, C$_{1\text{-}6}$ alkyl substituted with 0-3 R$^4$, wherein C$_{1\text{-}6}$ alkyl is selected from methyl, ethyl, propyl, i-propyl, butyl, isobutyl, t-butyl, pentyl, neopentyl, and hexyl;

R$^2$ is selected from phenyl substituted with 0-3 R$^5$ and a 5-10 membered heteroaryl system containing 1-4 heteroatoms substituted with 0-3 $R^5$, wherein the heteroaryl system is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridinyl, pyrimidinyl, pyrrolyl, quinazolinyl, quinolinyl, thiazolyl, thienyl, and tetrazolyl.

In another embodiment, the present invention provides novel compounds of formula (I), wherein $R^4$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{4a}R^{4a}$, $(CR'R')_rOH$, $(CR'R')_rOR^{4d}$, $(CR'R')_rSH$, $(CR'R')_rSR^{4d}$, $(CR'R')_rC(O)OH$, $(CR'R')_rC(O)R^{4b}$, $(CR'R')_rC(O)NR^{4a}R^{4a}$, $(CR'R')_rNR^{4f}C(O)R^{4b}$, $(CR'R')_rC(O)OR^{4d}$, $(CR'R')_rOC(O)R^{4b}$, $(CR'R')_rNR^{4f}C(O)OR^{4d}$, $(CR'R')_rOC(O)NR^{4a}R^{4a}$, $(CR'R')_rNR^{4a}C(O)NR^{4a}R^{4a}$, $(CR'R')_rS(O)_pR^{4b}$, $(CR'R')_rS(O)_2NR^{4a}R^{4a}$, $(CR'R')_rNR^{4f}S(O)_2R^{4b}$, $(CR'R')_rNR^{4f}S(O)_2NR^{4a}R^{4a}$, and $C_{1-6}$ haloalkyl, a $(CR'R')_r$ nonaromatic-heterocycle containing 1-4 heteroatoms substituted with 0-3 $R^{4e}$;

or alternatively, $R^4$, at each occurrence, is selected from $C_{1-8}$ alkyl, $C_{2-8}$ alkenyl, $C_{2-8}$ alkynyl, $(CR'R')_rC_{3-6}$ cycloalkyl substituted with 0-1 $R^{4e}$, Cl, Br, I, F, $NO_2$, CN, $(CR'R')_rNR^{4a}R^{4a}$, $(CR'R')_rOH$, $(CR'R')_rOR^{4d}$, $(CR'R')_rSH$, $(CR'R')_rSR^{4d}$, $(CR'R')_rC(O)OH$, $(CR'R')_rC(O)R^{4b}$, $(CR'R')_rC(O)NR^{4a}R^{4a}$, $(CR'R')_rNR^{4f}C(O)R^{4b}$, $(CR'R')_rC(O)OR^{4d}$, $(CR'R')_rOC(O)R^{4b}$, $(CR'R')_rNR^{4f}C(O)OR^{4d}$, $(CR'R')_rOC(O)NR^{4a}R^{4a}$, $(CR'R')_rNR^{4a}C(O)NR^{4a}R^{4a}$, $(CR'R')_rS(O)_pR^{4b}$, $(CR'R')_rS(O)_2NR^{4a}R^{4a}$, $(CR'R')_rNR^{4f}S(O)_2R^{4b}$, $(CR'R')_rNR^{4f}S(O)_2NR^{4a}R^{4a}$, and $C_{1-6}$ haloalkyl, a $(CR'R')_r$ nonaromatic-heterocycle containing 1-4 heteroatoms substituted with 0-3 $R^{4e}$;

alternatively, two $R^4$ on adjacent atoms join to form —O—$(CH_2)$—O—;

$R^{4a}$, at each occurrence, is independently selected from H, methyl, ethyl, propyl, i-propyl, butyl, s-butyl, i-butyl, t-butyl, pentyl, hexyl, allyl, propargyl, and a $(CH_2)_r$—$C_{3-6}$ cycloalkyl residue selected from cyclopropyl, cyclobutyl, cyclopentyl and cyclohexyl;

$R^{4b}$, at each occurrence, is selected from methyl, ethyl, propyl, i-propyl, butyl, s-butyl, i-butyl, t-butyl, pentyl, hexyl, allyl, propargyl, a $(CH_2)_r$—$C_{3-6}$ carbocyclic residue substituted with 0-3 $R^{4e}$, wherein the cycloalky residue is selected from cyclopropyl, cyclobutyl, cyclopentyl and cyclohexyl, and a $(CH_2)_r$-5-6 membered nonaromatic heterocyclic system containing 1-4 heteroatoms selected from N, O, and S, substituted with 0-2 $R^{4e}$;

$R^{4d}$, at each occurrence, is selected from H, methyl, $CF_3$, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, and $(CH_2)_r$phenyl;

$R^{4f}$, at each occurrence, is selected from H, methyl, ethyl, propyl, i-propyl, butyl, cyclopropyl, cyclobutyl, cyclopentyl and cyclohexyl;

$R^5$, at each occurrence, is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{5a}R^{5a}$, $(CR'R')_rOH$, $(CR'R')_rOR^{5d}$, $(CR'R')_rSH$, $(CR'R')_rC(O)H$, $(CR'R')_rSR^{5d}$, $(CR'R')_rC(O)OH$, $(CR'R')_rC(O)R^{5b}$, $(CR'R')_rC(O)NR^{5a}R^{5a}$, $(CR'R')_rNR^{5f}C(O)R^{5b}$, $(CR'R')_rC(O)OR^{5d}$, $(CR'R')_rOC(O)R^{5b}$, $(CR'R')_rNR^{5f}C(O)OR^{5d}$, $(CR'R')_rOC(O)NR^{5a}R^{5a}$, $(CR'R')_rNR^{5a}C(O)NR^{5a}R^{5a}$, $(CR'R')_rNR^{7a}C(O)NR^{7a}R^{7a}$, $(CR'R')_rNR^{7a}C(O)O(CR'R')_rR^{7d}$, $(CR'R')_rS(O)_pR^{5b}$, $(CR'R')_rS(O)_2NR^{5a}R^{5a}$, $(CR'R'')_rNR^{5f}S(O)_2R^{5b}$, $C_{1-6}$ haloalkyl, and $(CHR')_r$phenyl substituted with 0-3 $R^{5e}$, a $(CRR)_r$-5-10 membered heterocyclic system containing 1-4 heteroatoms selected from N, O, and S, substituted with 0-2 $R^{5c}$,

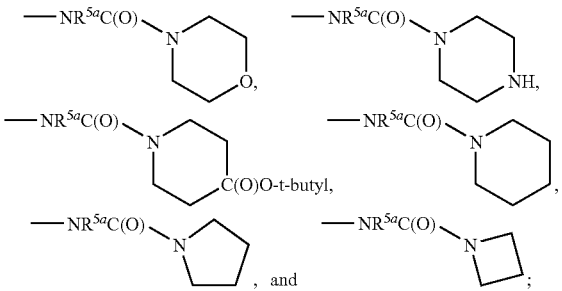

alternatively, two $R^5$ on adjacent atoms join to form —O—$(CH_2)$—O—;

$R^{5a}$, at each occurrence, is independently selected from H, methyl, ethyl, propyl, i-propyl, butyl, s-butyl, i-butyl, t-butyl, pentyl, hexyl, allyl, propargyl, and a $(CH_2)_r$—$C_{3-10}$ carbocyclic residue substituted with 0-1 $R^{5e}$, wherein the carbocyclic residue is selected from cyclopropyl, cyclobutyl, cyclopentyl, cyclohexyl, phenyl and naphthyl;

$R^{5b}$, at each occurrence, is selected from methyl, ethyl, propyl, i-propyl, butyl, s-butyl, i-butyl, t-butyl, pentyl, hexyl, allyl, propargyl, a $(CH_2)_r$—$C_{3-6}$ carbocyclic residue selected from cyclopropyl, cyclobutyl, cyclopentyl, cyclohexyl, and phenyl; and a $(CH_2)_r$-5-6 membered heterocyclic system containing 1-4 heteroatoms selected from N, O, and S, wherein the heterocyclic system is selected from pyridinyl, thiophenyl, furanyl, indazolyl, azetidinyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, morphlinyl, piperidinyl, pyrrolyl, 2,5-dihydropyrrolyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{5d}$, at each occurrence, is selected from H, methyl, $CF_3$, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, and $(CH_2)_r$phenyl;

or alternatively, $R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, $(CH_2)_r$OH, OH, SH, $C(O)OH$, $C(O)NHR^{5h}$, $C(O)OC_{1-5}$ alkyl, $(CH_2)_rSC_{1-5}$ alkyl, $(CH_2)_rNR^{5f}R^{5f}$, $(CH_2)_rC(O)NHSO_2$—$R^{5h}$, $NHSO_2R^{5h}$, and $(CH_2)_r$phenyl, $(CH_2)_r$tetrazolyl; and $R^{5f}$, at each occurrence, is selected from H, methyl, ethyl, propyl, i-propyl, butyl, and cyclopropyl, cyclobutyl, and phenyl.

In another embodiment, the present invention provides novel compounds of formula (I), wherein $R^5$, at each occurrence, is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_r$ $NR^{5a}R^{5a}$, $(CH_2)_rOH$, $(CH_2)_rOR^{5d}$, $(CH_2)_rSH$, $(CH_2)_rC(O)H$, $(CH_2)_rSR^{5d}$, $(CH_2)_rC(O)OH$, $(CH_2)_rC(O)R^{5b}$, $(CH_2)_rC(O)NR^{5a}R^{5a}$, $(CH_2)_rNR^{5f}C(O)R^{5b}$, $(CH_2)_rC(O)OR^{5d}$, $(CH_2)_rOC(O)R^{5b}$, $(CH_2)_rNR^{5f}C(O)OR^{5d}$, $(CH_2)_rOC(O)NR^{5a}R^{5a}$, $(CH_2)_rNR^{5a}C(O)NR^{5a}R^{5a}$, $(CH_2)_rNR^{7a}C(O)NR^{7a}R^{7a}$, $(CH_2)_rNR^{7a}C(O)O(CH_2)_rR^{7d}$, $(CH_2)_rS(O)_pR^{5b}$, $(CH_2)_rS(O)_2NR^{5a}R^{5a}$, $(CH_2)_rNR^{5f}S(O)_2R^{5b}$, $C_{1-6}$ haloalkyl, and $(CHR')_r$phenyl substituted with 0-3 $R^{5e}$,

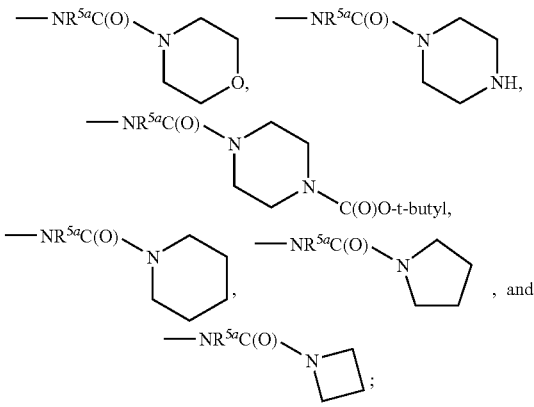

$R^{12}$ is selected from H and methyl.

In another embodiment, the present invention provides novel compounds of formula (I), wherein Z is selected from a bond, $-NR^{18}C(O)-$, $-NR^{18}-$, $-C(O)NR^{18}-$, and $-NHC(O)NH-$;

$R^2$ is phenyl substituted with 0-2 $R^5$;

$R^3$ is selected from $(CRR)_qOH$, $(CRR)_qOR^{3d}$, $(CH_2)_rC(O)OH$, $(CH_2)_rC(O)NR^{3a}R^{3d}$, $(CHR)_rC(O)NR^{3a}OR^{3d}$, $(CH_2)_rC(O)R^{3b}$, $(CH_2)_rC(O)OR^{3d}$, and $(CH_2)_r$-phenyl;

$R^{3a}$ is selected from H, methyl, ethyl, propyl, i-propyl, butyl, i-butyl, s-butyl, t-butyl, allyl, $CH_2CF_3$, $C(CH_3)CH_2CH_2OH$, cyclopropyl, 1-methylcyclopropyl, cyclobutyl, cyclopentyl, cyclohexyl, phenyl, and benzyl;

$R^{3b}$ is selected from pyrrolidinyl, pyrrolid-3-enyl, and morpholinyl;

$R^{3d}$ is selected from methyl, ethyl, propyl, i-propyl, butyl, i-butyl, t-butyl and benzyl;

R is selected from H, methyl, ethyl, propyl, i-propyl, butyl, i-butyl, s-butyl, pentyl, neopentyl, $(CH_2)_r$phenyl substituted with 0-1 $R^{3e}$;

$R^4$ is selected from methyl, ethyl, propyl, i-propyl, butyl, ethylene, $OCH_3$, $OCF_3$, $SCH_3$, $SO_2CH_3$, Cl, F, Br, CN;

$R^5$ is selected from methyl, ethyl, propyl, i-propyl, butyl, i-butyl, s-butyl, pentyl, hexyl, $CF_3$, $CF_2CF_3$, $CF_2H$, $OCF_3$, Cl, Br, I, F, $SCF_3$, $NR^{5a}R^{5a}$, $NHC(O)OR^{5a}$, $NHC(O)R^{5b}$, and $NHC(O)NHR^{5a}$; and $R^6$ is selected from H, methyl, ethyl, propyl, i-propyl, butyl, t-butyl, $C(O)OCH_3$, $C(O)NHCH_2CH_3$;

$R^7$ is H;

$R^{16}$ is selected from H and methyl;

$R^{17}$ is selected from H and methyl;

m is 0 l is 0 r is 0, 1 or 2; and q is 1.

In another embodiment, the present invention provides novel compounds of formula (I), wherein Z is a bond; and $R^2$ is a 5-10 membered heteroaryl system containing 1-4 heteroatoms selected from N, O, and S, substituted with 0-3 $R^5$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, the present invention provides novel compound of formula (I), wherein Z is a bond or $-NH-$; and $R^2$ is a 5-10 membered heteroaryl system containing 1-4 heteroatoms selected from N, O, and S, substituted with 0-3 $R^5$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, pyrrolotriazinyl, quinazolinyl, quinolinyl, thiazolyl, thienyl, and tetrazolyl.

In another embodiment, the present invention provides novel compounds of formula (I), wherein Z is selected from a bond, $-C(O)-$, $-C(O)NR^{15}-$, and $-NR^{15}C(O)-$;

$R^2$ is selected from phenyl substituted with 0-5 $R^5$ and a 5-10 membered heteroaryl system containing 1-4 heteroatoms selected from N, O, and S, wherein the heteroaryl system is selected from benzimidazolyl, benzooxazolyl, benzothiazolyl, the heteroaryl being substituted with 0-3 $R^5$;

$R^3$ is selected from $(CRR)_qOH$, $(CRR)_qSH$, $(CRR)_qOR^{3d}$, and $(CRR)_rC(O)R^{3b}$;

$R^{3b}$, at each occurrence, is independently selected from $C_{1-6}$ alkyl substituted with 0-3 $R^{3e}$, $C_{2-8}$ alkenyl substituted with 0-3 $R^{3e}$, $C_{2-8}$ alkynyl substituted with 0-3 $R^{3e}$, a $(CH_2)_r$-$C_{3-6}$ carbocyclic residue substituted with 0-2 $R^{3e}$, and a $(CH_2)_r$-5-6 membered heterocyclic system containing 1-4 heteroatoms selected from N, O, and S, substituted with 0-3 $R^{3e}$;

$R^{3d}$, at each occurrence, is independently selected from H, methyl, $-CF_3$, $C_{2-6}$ alkyl substituted with 0-3 $R^{3e}$, $C_{3-6}$ alkenyl substituted with 0-3 $R^{3e}$, $C_{3-6}$ alkynyl substituted with 0-3 $R^{3e}$, a $C_{3-10}$ carbocyclic residue substituted with 0-3 $R^{3e}$, and a $(CH_2)_r$-5-6 membered heterocyclic system containing 1-4 heteroatoms selected from N, O, and S, substituted with 0-3 $R^{3e}$;

$R^{3e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{3f}R^{3f}$, and $(CH_2)_r$phenyl;

$R^{3f}$, at each occurrence, is selected from H, $C_{1-6}$ alkyl, and $C_{3-6}$ cycloalkyl;

n is 1;

l is 0; and m is 0.

In another embodiment, the present invention provides novel compounds of formula (I), wherein Z is selected from a bond, $-C(O)-$, $-C(O)NR^{15}-$, and $-NR^{15}C(O)-$;

$R^2$ is selected from phenyl substituted with 0-5 $R^5$ and a 5-10 membered heteroaryl system containing 1-4 heteroatoms selected from N, O, and S, wherein the heteroaryl system is selected from quinazolinyl, triazinyl, pyrimidinyl, picolinyl, isonicotinyl, furanyl, indolyl, pyridinyl, pyrazolyl, pyrazinyl, thiazolyl, thiophenyl, and isoxazolyl the heteroaryl being substituted with 0-3 $R^5$;

$R^3$ is selected from $(CRR)_qOH$, $(CRR)_qSH$, $(CRR)_qOR^{3d}$, and $(CRR)_rC(O)R^{3b}$;

$R^{3b}$, at each occurrence, is independently selected from $C_{1-6}$ alkyl substituted with 0-3 $R^{3e}$, $C_{2-8}$ alkenyl substituted with 0-3 $R^{3e}$, $C_{2-8}$ alkynyl substituted with 0-3 $R^{3e}$, a $(CH_2)_r$—$C_{3-6}$ carbocyclic residue substituted with 0-2 $R^{3e}$, and a $(CH_2)_r$-5-6 membered heterocyclic system containing 1-4 heteroatoms selected from N, O, and S, substituted with 0-3 $R^{3e}$;

$R^{3d}$, at each occurrence, is independently selected from H, methyl, —$CF_3$, $C_{2-6}$ alkyl substituted with 0-3 $R^{3e}$, $C_{3-6}$ alkenyl substituted with 0-3 $R^{3e}$, $C_{3-6}$ alkynyl substituted with 0-3 $R^{3e}$, a $C_{3-10}$ carbocyclic residue substituted with 0-3 $R^{3e}$, and a $(CH_2)_r$-5-6 membered heterocyclic system containing 1-4 heteroatoms selected from N, O, and S, substituted with 0-3 $R^{3e}$;

$R^{3e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$$SC_{1-5}$ alkyl, $(CH_2)_rNR^{3f}R^{3f}$, and $(CH_2)_r$phenyl;

$R^{3f}$, at each occurrence, is selected from H, $C_{1-6}$ alkyl, and $C_{3-6}$ cycloalkyl;

n is 1;

l is 0; and m is 0.

In another embodiment, the present invention provides novel compounds of formula (I), wherein the compound is selected from the compounds of the examples.

In another embodiment, the present invention is directed to a pharmaceutical composition, comprising a pharmaceutically acceptable carrier and a therapeutically effective amount of a compound of Formula (I).

In another embodiment, the present invention is directed to a method for modulation of chemokine or chemokine receptor activity comprising administering to a patient in need thereof a therapeutically effective amount of a compound of Formula (I).

In another embodiment, the present invention is directed to a method for modulation of CCR-2 receptor activity comprising administering to a patient in need thereof a therapeutically effective amount of a compound of Formula (I).

In another embodiment, the present invention is directed to a method for modulation of MCP-1, MCP-2, MCP-3 and MCP-4, and MCP-5 activity that is mediated by the CCR2 receptor comprising administering to a patient in need thereof a therapeutically effective amount of a compound of Formula (I).

In another embodiment, the present invention is directed to a method for modulation of MCP-1 activity comprising administering to a patient in need thereof a therapeutically effective amount of a compound of Formula (I).

In another embodiment, the present invention is directed to a method for treating disorders, comprising administering to a patient in need thereof a therapeutically effective amount of a compound of Formula (I), said disorders being selected from osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer.

In another embodiment, the present invention is directed to a method for treating disorders, comprising administering to a patient in need thereof a therapeutically effective amount of a compound of Formula (I), wherein said disorders being selected from psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer.

In another embodiment, the present invention is directed to a method for treating disorders, comprising administering to a patient in need thereof a therapeutically effective amount of a compound of Formula (I), wherein said disorders being selected from alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer.

In another embodiment, the present invention is directed to a method for treating disorders, comprising administering to a patient in need thereof a therapeutically effective amount of a compound of Formula (I), wherein said disorders being selected from asthma, multiple sclerosis, artherosclerosis, and rheumatoid arthritis.

In another embodiment, the present invention is directed to a method for treating disorders, comprising administering to a patient in need thereof a therapeutically effective amount of a compound of Formula (I), wherein said disorders being selected from restinosis, organ transplantation, and cancer.

In another embodiment, the present invention is directed to a method for treating rheumatoid arthritis, comprising administering to a patient in need thereof a therapeutically effective amount of a compound of Formula (I).

In another embodiment, the present invention is directed to a method for treating multiple sclerosis, comprising administering to a patient in need thereof a therapeutically effective amount of a compound of Formula (I).

In another embodiment, the present invention is directed to a method for treating atherosclerosis, comprising administering to a patient in need thereof a therapeutically effective amount of a compound of Formula (I).

In another embodiment, the present invention is directed to a method for treating asthma, comprising administering to a patient in need thereof a therapeutically effective amount of a compound of Formula (I).

In another embodiment, the present invention is directed to a method for treating restinosis, comprising administering to a patient in need thereof a therapeutically effective amount of a compound of Formula (I).

In another embodiment, the present invention is directed to a method for treating organ transplantation, comprising administering to a patient in need thereof a therapeutically effective amount of a compound of Formula (I).

In another embodiment, the present invention is directed to a method for treating cancer, comprising administering to a patient in need thereof a therapeutically effective amount of a compound of Formula (I).

In another embodiment, the present invention is directed to a method for treating inflammatory diseases, comprising administering to a patient in need thereof a therapeutically effective amount of a compound of Formula (I).

In another embodiment, the present invention is directed to a method for treating inflammatory diseases which are at least partially mediated by CCR-2, comprising administering to a patient in need thereof a therapeutically effective amount of a compound of Formula (I).

In another embodiment, the present invention is directed to a method for modulation of CCR2 activity comprising administering to a patient in need thereof a therapeutically effective amount of a compound of Formula (I).

In another embodiment, the present invention is directed the use of a compound of Formula (I) in the preparation of a medicament for the treatment of osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a compound of formula (I) for use in therapy.

In another embodiment, $R^7$, $R^8$, $R^9$, and $R^{11}$ are H; $R^{10}$ is selected from H and methyl; $R^{16}$ is selected from H and methyl; $R^{17}$ is selected from H and methyl; m is 0 or 1; and l is 0 or 1.

In another embodiment, $R^1$ is selected from H, $C_{1-6}$ alkyl substituted with 0-3 $R^4$, wherein $C_{1-6}$ alkyl is selected from methyl, ethyl, propyl, i-propyl, butyl, t-butyl, pentyl, and hexyl.

In another embodiment, Z is selected from a bond and —C(O)NR$^{18}$—, —NR$^{18}$—, —NR$^{18}$C(O)—.

In another embodiment, Z is —C(O)NR$^{18}$—.

In another embodiment, Z is —NR$^{18}$—.

In another embodiment, Z is —NR$^{18}$C(O)—.

In another embodiment, $R^3$ is selected from (CRR)$_q$OH, (CRR)$_q$SH, (CRR)$_q$OR$^{3d}$, (CRR)$_q$S(O)$_p$R$^{3d}$, (CRR)$_r$C(O)R$^{3b}$, (CRR)$_q$NR$^{3a}$R$^{3a}$, (CRR)$_r$C(O)NR$^{3a}$R$^{3a}$, (CRR)$_r$C(O)NR$^{3a}$OR$^{3d}$, (CRR)$_q$SO$_2$NR$^{3a}$R$^{3a}$, (CRR)$_r$C(O)OR$^{3d}$, a (CRR)$_r$—C$_{3-10}$ carbocyclic residue substituted with 0-5 $R^{3e}$, and a (CRR)$_r$-5-10 membered heterocyclic system containing 1-4 heteroatoms selected from N, O, and S, substituted with 0-3 $R^{3e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

alternatively, $R^3$ and $R^{12}$ join to form a $C_{3-6}$ cycloalkyl substituted with 0-2 $R^{3g}$, a $C_{5-6}$ lactam substituted with 0-2 $R^{3g}$, or a $C_{5-6}$ lactone substituted with 0-2 $R^{3g}$.

In another embodiment, $R^3$ is selected from (CRR)$_q$OH, (CRR)$_q$OR$^{3d}$, (CH$_2$)$_r$C(O)OH, (CH$_2$)$_r$C(O)NR$^{3a}$R$^{3a}$, (CHR)$_r$C(O)NR$^{3a}$OR$^{3d}$, (CH$_2$)C(O)R$^{3b}$, (CH$_2$)$_r$C(O)OR$^{3d}$, and (CH$_2$)-phenyl.

In another embodiment, $R^3$ is selected from (CRR)$_q$OH, (CRR)$_q$OR$^{3d}$, (CH$_2$)$_r$C(O)OH, (CH$_2$)$_r$C(O)NR$^{3a}$R$^{3a}$, (CHR)$_r$C(O)NR$^{3a}$OR$^{3d}$, (CH$_2$)C(O)R$^{3b}$, and (CH$_2$)$_r$C(O)OR$^{3d}$.

In another embodiment, $R^6$ is selected from H, $C_{1-6}$ alkyl, (CRR)$_q$OH, (CRR)$_q$SH, (CRR)$_q$OR$^{6d}$, (CRR)$_q$S(O)$_p$R$^{6d}$, (CRR)$_r$C(O)R$^{6b}$, (CRR)$_q$NR$^{6a}$R$^{6a}$, (CRR)$_r$C(O)NR$^{6a}$R$^{6a}$, (CRR)$_r$C(O)NR$^{6a}$OR$^{6d}$, (CRR)$_q$SO$_2$NR$^{6a}$R$^{6a}$, (CRR)$_r$C(O)OR$^{6d}$, a (CRR)$_r$—C$_{6-10}$ carbocyclic residue substituted with 0-5 $R^{6e}$, and a (CRR)$_r$-5-10 membered heterocyclic system containing 1-4 heteroatoms selected from N, O, and S, substituted with 0-6 $R^{6e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,6-triazolyl, tetrazolyl, thiadiazolyl, thiazolyl, oxazolyl, pyrazinyl, and pyrimidinyl.

In another embodiment, $R^6$ is selected from H.

In another embodiment, $R^2$ is selected from phenyl substituted with 0-3 $R^5$ and a 5-10 membered heteroaryl system containing 1-4 heteroatoms substituted with 0-3 $R^5$, wherein the heteroaryl system is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^2$ is phenyl substituted with 0-2 $R^5$.

In another embodiment, $R^4$, at each occurrence, is selected from $C_{1-8}$ alkyl, $C_{2-8}$ alkenyl, $C_{2-8}$ alkynyl, (CR'R')$_r$C$_{3-6}$ cycloalkyl, Cl, Br, I, F, NO$_2$, CN, (CR'R')$_r$NR$^{4a}$R$^{4a}$, (CR'R')$_r$OH, (CR'R')$_r$OR$^{4d}$, (CR'R')$_r$SH, (CR'R')$_r$SR$^{4d}$, (CR'R')$_r$C(O)OH, (CR'R')$_r$C(O)R$^{4b}$, (CR'R')$_r$C(O)NR$^{4a}$R$^{4a}$, (CR'R')$_r$NR$^{4f}$C(O)R$^{4b}$, (CR'R')$_r$C(O)OR$^{4d}$, (CR'R')$_r$OC(O) R$^{4b}$, (CR'R')$_r$NR$^{4f}$C(O)OR$^{4d}$, (CR'R')$_r$OC(O)NR$^{4a}$R$^{4a}$, (CR'R')$_r$NR$^{4a}$C(O)NR$^{4a}$R$^{4a}$, (CR'R')$_r$S(O)$_p$R$^{4b}$, (CR'R')$_r$S (O)$_2$NR$^{4a}$R$^{4a}$, (CR'R')$_r$NR$^{4f}$S(O)$_2$R$^{4b}$, (CR'R')$_r$NR$^{4f}$S(O)$_2$ NR$^{4a}$R$^{4a}$, $C_{1-6}$ haloalkyl, and a (CR'R')$_r$nonaromatic-heterocycle containing 1-4 heteroatoms substituted with 0-3 $R^{4e}$; alternatively, two $R^4$ on adjacent atoms join to form —O—(CH$_2$)—O—;

$R^{4a}$, at each occurrence, is independently selected from H, methyl, ethyl, propyl, i-propyl, butyl, s-butyl, i-butyl, t-butyl, pentyl, hexyl, allyl, propargyl, and a (CH$_2$)$_r$—C$_{3-6}$ cycloalkyl residue selected from cyclopropyl, cyclobutyl, cyclopentyl and cyclohexyl;

$R^{4b}$, at each occurrence, is selected from methyl, ethyl, propyl, i-propyl, butyl, s-butyl, i-butyl, t-butyl, pentyl, hexyl, allyl, propargyl, a (CH$_2$)$_r$—C$_{3-6}$ carbocyclic residue substituted with 0-3 $R^{4e}$, wherein the cycloalky residue is selected from cyclopropyl, cyclobutyl, cyclopentyl and cyclohexyl, and a (CH$_2$)$_r$-5-6 membered nonaromatic heterocyclic system containing 1-4 heteroatoms selected from N, O, and S, substituted with 0-2 $R^{4e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{4d}$, at each occurrence, is selected from H, methyl, CF$_3$, ethyl, propyl, i-propyl, butyl, s-butyl, i-butyl, t-butyl, pentyl, hexyl, allyl, propargyl, and a (CH$_2$)$_r$—C$_{3-6}$ carbocyclic residue selected from cyclopropyl, cyclobutyl, cyclopentyl and cyclohexyl;

$R^{4e}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, and (CH$_2$)$_r$phenyl;

$R^{4f}$, at each occurrence, is selected from H, methyl, ethyl, propyl, i-propyl, butyl, cyclopropyl, cyclobutyl, cyclopentyl and cyclohexyl.

In another embodiment, $R^4$ is selected from methyl, ethyl, propyl, i-propyl, butyl, ethylene, OCH$_3$, OCF$_3$, SCH$_3$, SO$_2$CH$_3$, Cl, F, Br, and CN.

In another embodiment, $R^5$, at each occurrence, is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{5a}R^{5a}$, $(CR'R')_rOH$, $(CR'R')_rOR^{5d}$, $(CR'R')_rSH$, $(CR'R')_rC(O)H$, $(CR'R')_rSR^{5d}$, $(CR'R')_rC(O)OH$, $(CR'R')_rC(O)R^{5b}$, $(CR'R')_rC(O)NR^{5a}R^{5a}$, $(CR'R')_rNR^{5f}C(O)R^{5b}$, $(CR'R')_rC(O)OR^{5d}$, $(CR'R')_rOC(O)R^{5b}$, $(CR'R')_rNR^{5f}C(O)OR^{5d}$, $(CR'R')_rOC(O)NR^{5a}R^{5a}$, $(CR'R')_rNR^{5a}C(O)NR^{5a}R^{5a}$, $(CR'R')_rNR^{7a}C(O)NR^{7a}R^{7a}$, $(CR'R')_rNR^{7a}C(O)O(CR'R')_rR^{7d}$, $(CR'R')_rS(O)_pR^{5b}$, $(CR'R')_rS(O)_2NR^{5a}R^{5a}$, $(CR'R')_rNR^{5f}S(O)_2R^{5b}$, $C_{1-6}$ haloalkyl, and $(CHR')_rphenyl$ substituted with 0-3 $R^{5e}$;

alternatively, two $R^5$ on adjacent atoms join to form —O—$(CH_2)$—O—;

$R^{5a}$, at each occurrence, is independently selected from H, methyl, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{5b}$, at each occurrence, is selected from methyl, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{5d}$, at each occurrence, is selected from H, methyl, $CF_3$, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4}R^{4f}$, and $(CH_2)_rphenyl$; and $R^{5f}$, at each occurrence, is selected from H, methyl, ethyl, propyl, i-propyl, butyl, and cyclopropyl, cyclobutyl, and phenyl.

In another embodiment, $R^5$, at each occurrence, is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{5a}R^{5a}$, $(CR'R')_rOH$, $(CR'R')_rOR^{5d}$, $(CR'R')_rSH$, $(CR'R')_rC(O)H$, $(CR'R')_rSR^{5d}$, $(CR'R')_rC(O)OH$, $(CR'R')_rC(O)R^{5b}$, $(CR'R')_rC(O)NR^{5a}R^{5a}$, $(CR'R')_rNR^{5f}C(O)R^{5b}$, $(CR'R')_rC(O)OR^{5d}$, $(CR'R')_rOC(O)R^{5b}$, $(CR'R')_rNR^{5f}C(O)OR^{5d}$, $(CR'R')_rOC(O)NR^{5a}R^{5a}$, $(CR'R')_rNR^{5a}C(O)NR^{5a}R^{5a}$, $(CR'R')_rNR^{7a}C(O)NR^{7a}R^{7a}$, $(CR'R')_rNR^{7a}C(O)O(CR'R')_rR^{7d}$, $(CR'R')_rS(O)_pR^{5b}$, $(CR'R')_rS(O)_2NR^{5a}R^{5a}$, $(CR'R'')_rNR^{5f}S(O)_2R^{5b}$, $C_{1-6}$ haloalkyl, and $(CHR')_rphenyl$ substituted with 0-3 $R^{5e}$, a $(CRR)_r$-5-10 membered heterocyclic system containing 1-4 heteroatoms selected from N, O, and S, substituted with 0-2 $R^{5c}$,

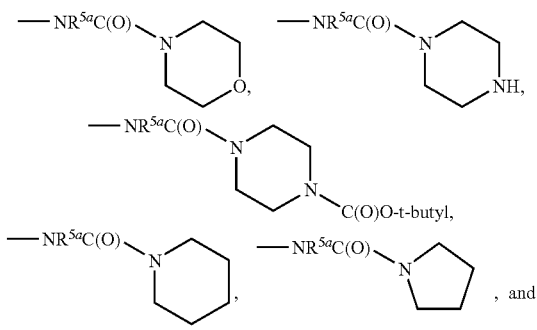

-continued

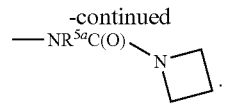

In another embodiment, $R^5$, at each occurrence, is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_rNR^{5a}R^{5a}$, $(CH_2)_rOH$, $(CH_2)_rOR^{5d}$, $(CH_2)_rSH$, $(CH_2)_rC(O)H$, $(CH_2)_rSR^{5d}$, $(CH_2)_rC(O)OH$, $(CH_2)_rC(O)R^{5b}$, $(CH_2)_rC(O)NR^{5a}R^{5a}$, $(CH_2)_rNR^{5f}C(O)R^{5b}$, $(CH_2)_rC(O)OR^{5d}$, $(CH_2)_rOC(O)R^{5b}$, $(CH_2)_rNR^{5f}C(O)OR^{5d}$, $(CH_2)_rOC(O)NR^{5a}R^{5a}$, $(CH_2)_rNR^{5a}C(O)NR^{5a}R^{5a}$, $(CH_2)_rNR^{7a}C(O)NR^{7a}R^{7a}$, $(CH_2)_rNR^{7a}C(O)O(CH_2)_rR^{7d}$, $(CH_2)_rS(O)_pR^{5b}$, $(CH_2)_rS(O)_2NR^{5a}R^{5a}$, $(CH_2)_rNR^{5f}S(O)_2R^{5b}$, $C_{1-6}$ haloalkyl, and $(CHR')_rphenyl$ substituted with 0-3 $R^{5e}$,

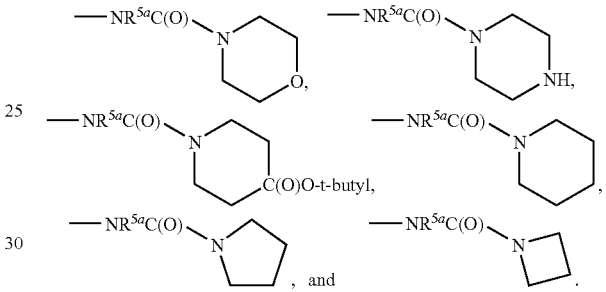

In another embodiment, $R^5$ is selected from methyl, ethyl, propyl, i-propyl, butyl, i-butyl, s-butyl, pentyl, hexyl, $CF_3$, $CF_2CF_3$, $CF_2H$, $OCF_3$, Cl, Br, I, F, $SCF_3$, $NR^{5a}R^{5a}$, $NHC(O)OR^{5a}$, $NHC(O)R^{5b}$, and $NHC(O)NHR^{5a}$.

In another embodiment, Z is a bond and $R^2$ is a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries and stereoisomers are considered to be a part of the present invention. When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602-2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R^{10}$) occurs more than one time in any constituent or formula for a compound, its definition at each occurrence is independent of its definition at every other occurrence. Thus, for example, if a group is shown to be substituted with 0-2 $R^{10}$, then said group may optionally be substituted with up to two $R^{10}$ groups and $R^{10}$ at each occurrence is selected independently from the definition of $R^{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

As used herein, the term "cyclic acetal" or the phrase when two variables "join to form a cyclic acetal" is intended to mean the substituent —O—CH$_2$—O—.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of formula 1.6, which contain a four-membered lactam, are derived from compounds of formula 1.1, the syntheses of which have been described previously (P. H. Carter, R. J. Cherney, WO-PCT 0250019, 2002, the contents of which are hereby incorporated by reference). As shown in Scheme 1, acid-mediated Boc removal, peptide coupling with the known serine derivative 1.2, and cyclization under Mitsonobu conditions (see G M Salituro and C A Townsend *J. Am. Chem. Soc.* 1990, 112, 760-770) provides the beta-lactam 1.4 from carbamate 1.1. Removal of the Ox protecting group (see G M Salituro and C A Townsend *J. Am. Chem. Soc.* 1990, 112, 760-770) provides a primary amine, which can be conjugated in a variety of ways well known to one skilled in the art. For example, reaction with an acid chloride will form an amide (Z=—NHC(O)—) and reaction with an isocyanate will form a urea (Z=—NHCONH—). Alternatively, the amine can be arylated (Z=—NH—), either using Pd catalysis (see D. Zim & S. L. Buchwald, Organic Letters 2003, 5, 2413 and T. Wang, D. R. Magnia, & L. G. Hamann, ibid, 897, and references cited therein) or through direct nucleophilic addition to the aromatic ring (e.g. to a 2-halopyridine). The resultant compounds 1.5 are transformed to compounds 1.6 through deprotection and reductive amination. If desired, compounds of formula 1.6 can be alkylated via a second reductive amination (not illustrated).

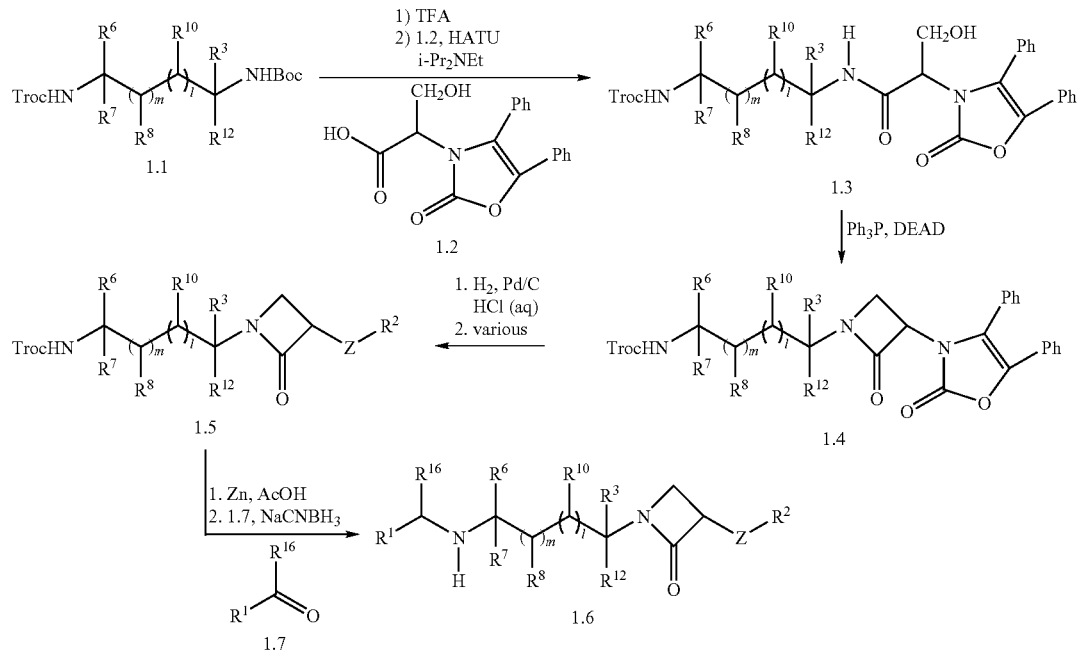

SCHEME 1

Compounds of formula 2.5, which contain a five-membered lactam, are synthesized as shown in Scheme 2. Acid-mediated Boc removal, peptide coupling with the known methionine derivative 2.1, sulfur alkylation, and intramolecular amide alkylation under basic conditions (Freidinger et al., *J. Org. Chem.* 1982, 47, 104) provides the gamma-lactam 2.3 from carbamate 1.1. Removal of the Boc protecting group provides a primary amine, which can be conjugated in a variety of ways well known to one skilled in the art. For example, reaction with an acid chloride will form an amide (Z=—CO—) and reaction with an isocyanate will form a urea (Z=—CONH—). Alternatively, the amine can be arylated (Z=—NH—), either using Pd catalysis (see D. Zim & S. L. Buchwald, *Organic Letters* 2003, 5, 2413 and T. Wang, D. R. Magnia, & L. G. Hamann, ibid, 897, and references cited therein) or through direct nucleophilic addition to the aromatic ring (e.g. to a 2-halopyridine). The resultant compounds 2.4 are transformed to compounds 2.5 through deprotection and reductive amination. If desired, compounds of formula 2.5 can be alkylated via a second reductive amination (not illustrated).

2001), ester hydrolysis, and intramolecular amide formation provides the delta-lactam 3.3 from carbamate 1.1. Removal of the Boc protecting group provides a primary amine, which can be conjugated in a variety of ways well known to one skilled in the art. For example, reaction with an acid chloride will form an amide (Z=—CO—) and reaction with an isocyanate will form a urea (Z=—CONH—). Alternatively, the amine can be arylated (Z=—NH—), either using Pd catalysis (see D. Zim & S. L. Buchwald, *Organic Letters* 2003, 5, 2413 and T. Wang, D. R. Magnia, & L. G. Hamann, ibid, 897, and references cited therein) or through direct nucleophilic addition to the aromatic ring (e.g. to a 2-halopyridine). The result-

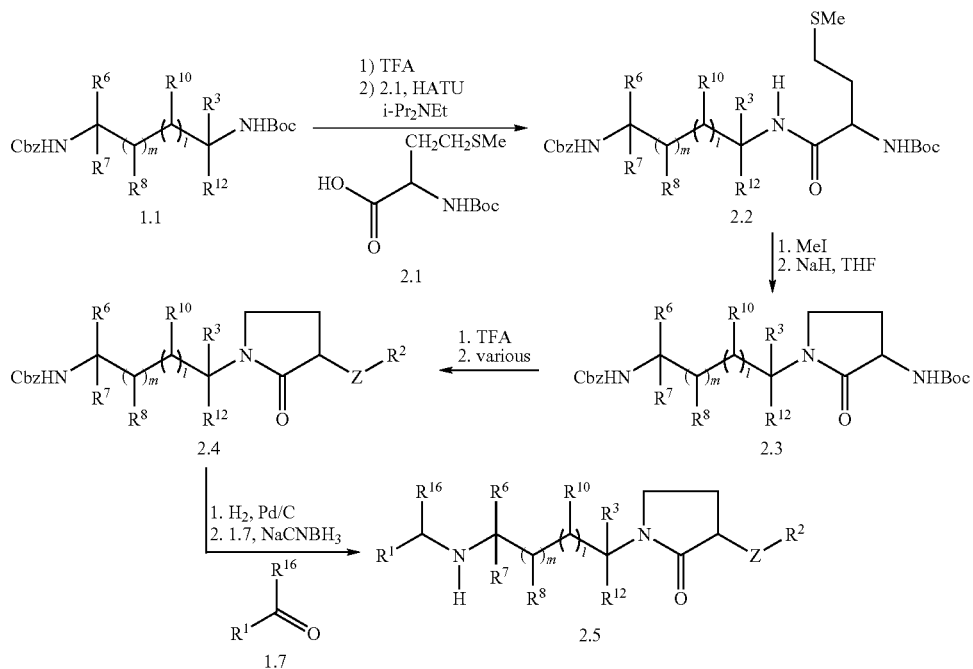

SCHEME 2

Compounds of formula 3.5, which contain a six-membered lactam, are synthesized as shown in Scheme 3. Acid-mediated Boc removal, reductive amination with the known glutamic acid derivative 3.1 (X. Zhang, W. Han, WO PCT 0164678, ant compounds 3.4 are transformed to compounds 3.5 through deprotection and reductive amination. If desired, compounds of formula 3.5 can be alkylated via a second reductive amination (not illustrated).

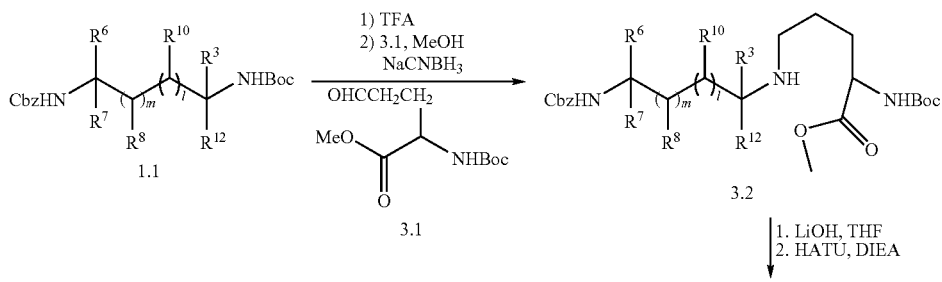

SCHEME 3

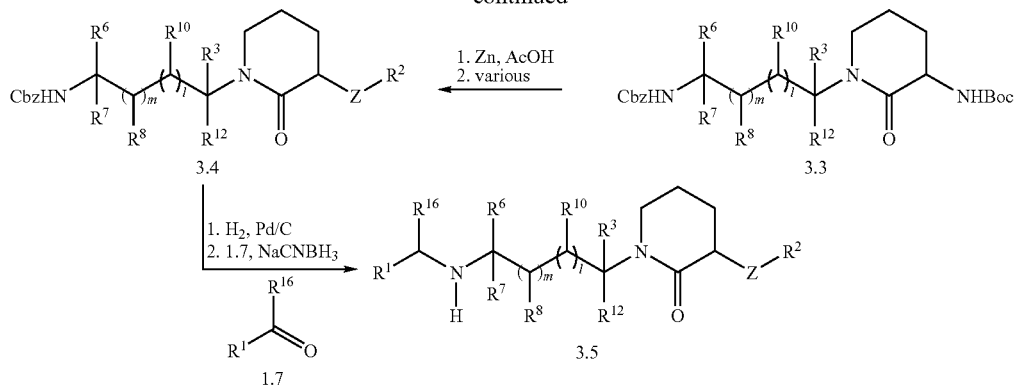

Copending patent applications, all filed on Aug. 19, 2004, disclose additional chemokine receptor antagonists. These three applications are hereby incorporated by reference in their entirety: "N-ALKYLATED DIAMINOPROPANE DERIVATIVES AS MODULATORS OF CHEMOKINE RECEPTOR ACTIVITY", "SUBSTITUTED CYCLOALKYLAMINE DERIVATIVES AS MODULATORS OF CHEMOKINE RECEPTOR ACTIVITY", and "CYCLIC DERIVATIVES AS MODULATORS OF CHEMOKINE RECEPTOR ACTIVITY".

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

N-(2-(((S)-1-((2S,3S)-3-hydroxy-1-(isobutylamino) hexan-2-yl)-2-oxopyrrolidin-3-yl)carbamoyl)-4-(trifluoromethyl)phenyl)azetidine-1-carboxamide (1a) A solution of [1S,2S]-[1-(benzyloxycarbonylaminomethyl)-2-hydroxy-pent-3-ynyl]-carbamic acid tert-butyl ester (1.19 g, 3.29 mmol, prepared as described in WO PCT 0250019) was dissolved in CH$_2$Cl$_2$ (20 mL) and treated with TFA (10 mL). The solution was stirred for 3 h and then concentrated in vacuo. The residue was dissolved in CH$_2$Cl$_2$ and concentrated in vacuo; this procedure was repeated. The residue was dissolved in CH$_2$Cl$_2$ (30 mL). The resultant solution was charged sequentially with N, N-diisopropylethylamine (2.3 mL, 13.2 mmol), HOBt (466 mg, 3.45 mmol), N-Boc methionine (820 mg, 3.29 mmol), and BOP (1.53 g, 3.45 mmol). The reaction was stirred for 12 h and partitioned between EtOAc and sat. NH$_4$Cl. The organic phase was washed with sat. NaHCO$_3$ and brine, and then dried (Na$_2$SO$_4$), filtered, and concentrated in vacuo. The residue was purified by flash chromatography to afford [2S,3S]-[2-[(2S)-(2-tert-butoxycarbonylamino-4-methylsulfanyl-butyrylamino)]-3-hydroxy-hex-4-ynyl]-carbamic acid benzyl ester (1.27 g, 78% yield). MS found: (M+Na)$^+$=516.3.

(1b) The compound (2S,3S)-[2-[(2S)-(2-tert-butoxycarbonylamino-4-methylsulfanyl-butyrylamino)]-3-hydroxy-hex-4-ynyl]-carbamic acid benzyl ester (1.27 g, 2.6 mmol) was dissolved in 10:1 iodomethane/EtOAc (22 mL). The resultant solution was stirred for 65 h at RT, at which point a two-phase mixture had evolved. The mixture was treated with 1:1 CHCl$_3$/EtOAc until dissolution was achieved, and then the resultant solution was concentrated in vacuo. The residue was redissolved in 1:1 CHCl$_3$/EtOAc and concentrated in vacuo; this procedure was repeated to give the salt as a yellow solid. This material was dissolved in THF (45 mL). The resultant solution was cooled to 0° C., treated with sodium hydride (310 mg, 12.9 mmol), and stirred for 2 h at 0° C. The reaction was quenched with sat. NH$_4$Cl and extracted twice with EtOAc. The organic extracts were combined, washed with brine, dried (Na$_2$SO$_4$), filtered, and concentrated in vacuo. The crude residue was purified by flash chromatography to afford {(3S)-1-[(1S,2S)-1-(benzyloxycarbonylamino-methyl)-2-hydroxy-pent-3-ynyl]-2-oxo-pyrrolidin-3-yl}-carbamic acid tert-butyl ester (913 mg, 79% yield). MS found: (M+Na)$^+$=468.4.

(1c) A portion of the above compound (1b, 2.55 g, 68 mmol) was dissolved in CH$_2$Cl$_2$ (72 mL) and treated with TFA (35 mL). The solution was stirred for 3.5 h and then concentrated in vacuo. The residue was dissolved in CH$_2$Cl$_2$ and concentrated in vacuo; this procedure was repeated. A portion of this residue (0.83 g, 2.4 mmol) was dissolved in CH$_2$Cl$_2$ (40 mL). The resultant solution was charged sequentially with 2-(azetidinylcarbonyl)amino-5-trifluoromethylbenzoic acid (0.72 g, 2.5 mmol), BOP (1.2 g, 2.6 mmol), 4-dimethylaminopyridine (0.32 g, 2.6 mmol), and N,N-diisopropylethylamine (1.6 g, 12 mmol). The reaction was stirred for 12 h and partitioned between EtOAc and sat. NH$_4$Cl. The organic phase was washed with sat. NaHCO$_3$ and brine, and then dried (Na$_2$SO$_4$), filtered, and concentrated. The residue was purified by flash chromatography to afford (1S,2S,3S) [2-(3-{2-[(azetidine-1-carbonyl)-amino]-5-trifluoromethyl-benzoylamino}-2-oxo-pyrrolidin-1-yl)-3-hydroxy-hex-4-ynyl]-carbamic acid benzyl ester (0.15 g). MS found: (M+H)$^+$=616.2.

(1d) The above compound (1c, 150 mg, 0.24 mmol) was dissolved in MeOH (20 mL). The resultant solution was charged with 10% Pd/C, Degussa style (75 mg), stirred under H$_2$ (1 atm) for 6 h at RT, filtered, and concentrated in vacuo. A portion of the residue (51 mg, 0.1 mmol) was redissolved in dichloroethane (20 mL). The resultant solution was charged sequentially with isobutyraldehyde (7.2 mg, 0.1 mmol) and sodium triacetoxyborohydride (32 mg, 0.15 mmol), stirred for 1.5 h at RT, quenched with sat. NaHCO$_3$, and extracted twice with EtOAc. The organic extracts were combined, washed with brine, dried (Na$_2$SO$_4$), filtered, and concentrated in vacuo. The residue was purified by reverse-phase HPLC to afford the TFA salt of the title compound (26.6 mg) as a white powder after lyopholization. MS found: (M+H)$^+$=542.4.

Example 2

N-(2-(((S)-1-((2S,3S)-3-hydroxy-1-(neopentylamino)hexan-2-yl)-2-oxopyrrolidin-3-yl)carbamoyl)-4-(trifluoromethyl)phenyl)azetidine-1-carboxamide (2a) Trimethylacetaldehyde was incorporated into Example 1 (step 1d) to give the TFA salt of the title compound. MS found: (M+H)$^+$=556.4.

Example 3

N-((S)-1-((2S,3S)-3-hydroxy-1-(isobutylamino)hexan-2-yl)-2-oxopyrrolidin-3-yl)-3-(trifluoromethyl)benzamide (3a) N,N'-Dicyclohexylcarbodiimide (1.1 g, 5.3 mol) was added to a solution of α,α,α-trifluoro-m-toluic acid (1.0 g, 5.3 mmol) and pentafluorophenol (1.1 g, 5.8 mmol) in THF (10.0 mL). After stirring for 3.5 h, the solvent was removed under vacuum. The residue was dissolved in Et$_2$O (20 mL), filtered, and washed with brine (2×10 mL), dried over Na$_2$SO$_4$, filtered, and evaporated to dryness to provide compound perfluorophenyl 3-(trifluoromethyl)benzoate as a yellow oil (1.7 g, 90%): $^1$H NMR (300 MHz, CD$_3$OD) δ 8.51-8.39 (m, 2H), 8.09 (d, J=6.0 Hz, 1H), 7.88-7.79 (m, 1H); $^{19}$F NMR (282 MHz, CD$_3$OD) δ −64.9 (3F), −155.6 (2F), −165.7 (1F), −168.9 (2F).

(3b) A solution of {(3S)-1-[(1S,2S)-1-(benzyloxycarbonylamino-methyl)-2-hydroxy-pent-3-ynyl]-2-oxo-pyrrolidin-3-yl}-carbamic acid tert-butyl ester in CH$_2$Cl$_2$ (72 mL) was treated with TFA (35 mL). The solution was stirred for 3.5 h and then concentrated in vacuo.

The residue was dissolved in CH$_2$Cl$_2$ and concentrated in vacuo; this procedure was repeated. A portion of this residue (0.94 g) was dissolved in DMF (8 mL). The resultant solution was charged with perfluorophenyl 3-(trifluoromethyl)benzoate (0.73 g) and N,N-diisopropylethylamine (0.9 mL). The reaction was stirred for 14 h and concentrated in vacuo. The residue was dissolved in EtOAc and the organic phase was washed with 5% LiCl (2×10 mL), 1 M HCl (3×20 mL), water (30 mL), and brine (30 mL) before being dried (sodium sulfate), filtered, and concentrated in vacuo. The residue was purified by flash chromatography to afford benzyl (2S,3S)-3-hydroxy-2-((S)-2-oxo-3-(3-(trifluoromethyl)benzamido)pyrrolidin-1-yl)hex-4-ynylcarbamate (0.66 g). MS found: (M+H)$^+$=518.

(3c) A solution of benzyl (2S,3S)-3-hydroxy-2-((S)-2-oxo-3-(3-(trifluoromethyl)benzamido)pyrrolidin-1-yl)hex-4-ynylcarbamate (0.32 g) in MeOH (5 mL) was charged with 10% Pd/C and then stirred under H$_2$ (1 atm) for 5 h at RT, filtered through diatomaceous earth, and concentrated in vacuo to provide N-((S)-1-((2S,3S)-1-amino-3-hydroxyhexan-2-yl)-2-oxopyrrolidin-3-yl)-3-(trifluoromethyl)benzamide (0.24 g). MS found: (M+H)$^+$=388.

(3d) A solution of N-((S)-1-((2S,3S)-1-amino-3-hydroxyhexan-2-yl)-2-oxopyrrolidin-3-yl)-3-(trifluoromethyl)benzamide (0.12 g) in dichloroethane (2 mL) was charged sequentially with isobutyraldehyde (0.017 mL), acetic acid (2 mg), and sodium triacetoxyborohydride (130 mg). The mixture was stirred at RT for 2 h before being concentrated in vacuo. The residue was dissolved in ethyl acetate and the organic solution was washed with saturated sodium bicarbonate, water, and brine (10 mL) before being dried (sodium sulfate), filtered and concentrated in vacuo. Purification of the residue by RP-HPLC afforded the TFA salt of the title compound as a white powder (72 mg) after lyopholization. MS found: (M+H)$^+$=444.

Example 4

1-(2-(((S)-1-((2S,3S)-3-hydroxy-1-(isobutylamino)hexan-2-yl)-2-oxopyrrolidin-3-yl)carbamoyl)-4-(trifluoromethyl)phenyl)-3-ethylurea (4a) Following procedure 3a above, 2-(3-ethylureido)-5-(trifluoromethyl)benzoic acid (see WO PCT WO-02/50019) was converted to perfluorophenyl 2-(3-ethylureido)-5-(trifluoromethyl)benzoate (80% yield). This material was carried through procedures 3b, 3c, and 3d to afford the TFA salt of the title compound as a white powder after RP-HPLC and lyopholization. MS found: (M+H)$^+$=530.

Example 5

1-(2-(((S)-1-((2S,3S)-3-hydroxy-1-(isobutylamino)hexan-2-yl)-2-oxopyrrolidin-3-yl)carbamoyl)-4-(trifluoromethyl)phenyl)-3-isopropylurea (5a) Following procedure (3a), 2-(3-isopropylureido)-5-(trifluoromethyl)benzoic acid (see WO PCT WO-02/50019) was converted to perfluorophenyl 2-(3-isopropylureido)-5-(trifluoromethyl)benzoate (53% yield). This material was carried through procedures 3b, 3c, and 3d to afford the TFA salt of the title compound as a white powder after RP-HPLC and lyopholization. MS found: (M+H)$^+$=544.

Example 6

N-((S)-1-((2S,3S)-3-hydroxy-1-(neopentylamino)hexan-2-yl)-2-oxopyrrolidin-3-yl)-3-(trifluoromethyl)benzamide (6a) A sample of N-((S)-1-((2S,3S)-1-amino-3-hydroxyhexan-2-yl)-2-oxopyrrolidin-3-yl)-3-(trifluoromethyl)benzamide (see procedure 3c above) was carried through procedure 3d, substituting pivaldehyde for isobutyraldehyde, to afford the TFA salt of the title compound as a white powder after RP-HPLC and lyopholization. MS found: (M+H)$^+$=458.

TABLE OF EXAMPLES

The following table illustrates examples of the present invention. The data in the "MS" columns represent the values observed for the (M+H)$^+$ ions in electrospray mass spectroscopy experiments. The substituents listed in each table are to be paired with the structure embedded in the table heading. The synthesis of all of these compounds has been described in detail in the previous section (Examples).

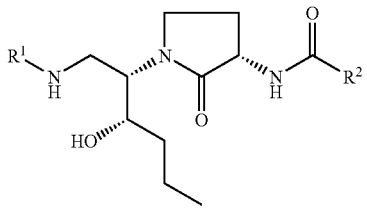

Ex 1-6

| Ex | R¹ | R² | MS m/z (M + H)⁺ |
|---|---|---|---|
| 1 | Isobutyl | 2-(azetidinylcarbonyl)amino-5-trifluoromethylphenyl | 542 |
| 2 | Neopentyl | 2-(azetidinylcarbonyl)amino-5-trifluoromethylphenyl | 556 |
| 3 | Isobutyl | 3-(trifluoromethyl)phenyl | 444 |
| 4 | Isobutyl | 3-ethylureido-5-(trifluoromethyl)phenyl | 530 |
| 5 | Isobutyl | 3-isopropylureido-5-(trifluoromethyl)phenyl | 544 |
| 6 | Neopentyl | 3-(trifluoromethyl)phenyl | 458 |

UTILITY

Compounds of formula I are shown to be modulators of chemokine receptor activity using assays know by those skilled in the art. In this section, we describe these assays and give their literature reference. By displaying activity in these assays of MCP-1 antagonism, compounds of formula I are expected to be useful in the treatment of human diseases associated with chemokines and their cognate receptors. The definition of activity in these assays is a compound demonstrating an $IC_{50}$ of 20 µM or lower in concentration when measured in a particular assay.

Antagonism of MCP-1 Binding to Human PBMC (Yoshimura et al., *J. Immunol.* 1990, 145, 292)

Compounds of the present invention have activity in the antagonism of MCP-1 binding to human PBMC (human peripheral blood mononuclear cells) described here.

Millipore filter plates (#MABVN1250) are treated with 100 µl of binding buffer (0.5% bovine serum albumin, 20 mM HEPES buffer and 5 mM magnesium chloride in RPMI 1640 media) for thirty minutes at room temperature. To measure binding, 50 µl of binding buffer, with or without a known concentration compound, is combined with 50 µl of $^{125}$-I labeled human MCP-1 (to give a final concentration of 150 pM radioligand) and 50 µl of binding buffer containing $5 \times 10^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-Induced Calcium Influx (Sullivan, et al. Methods Mol. Biol., 114, 125-133 (1999))

Compounds of the present invention have activity in the antagonism of MCP-1-induced calcium influx assay described here.

Calcium mobilization is measured using the fluorescent $Ca^{2+}$ indicator dye, Fluo-3. Cells are incubated at $8 \times 10^5$ cells/ml in phosphate-buffered saline containing 0.1% bovine serum albumin, 20 mM HEPES buffer, 5 mM glucose, 1% fetal bovine serum, 4 µM Fluo-3 AM and 2.5 mM probenecid for 60 minutes at 37° C. Cells used for such calcium assays can include human monocytes isolated as described by Weiner et al., J. Immunol. Methods, 36, 89-97 (1980) or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of $2-4 \times 10^6$ cells/ml. Cells are plated into 96-well, black-wall microplates (100 µl/well) and the plates centrifuged at 200×g for 5 minutes. Various concentrations of compound are added to the wells (50 µl/well) and after 5 minutes, 50 µl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-Induced Human PBMC Chemotaxis (Bacon et al., *Brit. J. Pharmacol.* 1988, 95, 966)

Compounds of the present invention have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1 \times 10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 µl to each well and there should be a positive meniscus after dispensing. The 8 micron filter is placed gently on top of the 96 well plate, a rubber gasket is attached to the bottom of the upper chamber, and the chamber is assembled. A 200 µl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

CCR5 Binding and Functional Assays

Cell derivation and cell culture: A pool of HT1080 cells stably expressing endogenous CC chemokine receptor 5 (CCR5) were developed using the methods outlined by Harrington, Sherf, and Rundlett (see U.S. Pat. Nos. 6,361,972 and U.S. Pat. No. 6,410,266). The highest-expressing clones were isolated using repetitive flow cytometry, followed by subcloning. These cells were then cultured in 6-well dishes at $3\times10^5$ cells/well and transfected with a DNA vector containing the chimeric HA-tagged G protein Gqi5 (Molecular Devices; 5 micrograms of linearized vector DNA in 15 microL of Ex-Gen from Fermentes was used for the transfection). Two days after transfection, the wells were combined and plated into P100 plates. Seven days after plating, colonies were picked, expanded, and analyzed for Gqi5 content by Western blot. A clone (designated as 3559.1.6) having high expression of Gqi5 (from transfection) and of CCR5 (endogenous) was selected and used for the experiments described below. The HT1080 cells (clone 3559.1.6) were cultured with alpha-MEM supplemented with 10% dialyzed fetal bovine serum, 2% penicillin/streptomycin/glutamine, and 500 microgram/mL hygromycin B (final concentration) at 37° C. with 5% $CO_2$ in a humidified atmosphere.

Membrane Preparation: A cell pellet containing $1\times10^8$ HT1080 cells (clone 3559.1.6) was resuspended in 5 mL of ice-cold Membrane Prep Buffer (50 mM HEPES, 5 mM $MgCl_2$, 1 mM $CaCl_2$) and homogenized at high-speed on a Polytron homogenizer for 20 sec on ice. The homogenate was diluted with another 25 mL of Membrane Prep Buffer and centrifuged for 12 min (48,000×g at 4° C.). The cell pellet was resuspended in 5 mL of Membrane Prep Buffer before being rehomogenized as described previously. The homogenate was diluted with 5 mL of Membrane Prep Buffer and assayed for CCR5 protein concentration.

Binding assay: The freshly-prepared homogenate from the Membrane Preparation described above was diluted in Binding buffer (50 mM HEPES, 5 mM $MgCl_2$, 1 mM $CaCl_2$, 0.1% BSA; one complete protease inhibitor tablet was added before assay) to achieve a final protein concentration of 10 micrograms/well (solid white 96-well plates from Corning, Inc.). This membrane preparation was mixed with WGA-SPA beads (Amerhsam; pre-soaked in Binding buffer) to give a concentration of 200 micrograms/well. The membrane/SPA bead mix (100 microliters/well) was then added to a plate that had been pre-dotted with 2 microliters DMSO containing various concentrations of test articles (pure DMSO for negative control; various concentrations of examples of this invention for test articles; 500 nM MIP-1 beta as a positive control). The binding assay was initiated through the addition of 50 microliters of $[^{125}I]$-MIP-1 beta (Perkin Elmer; material was diluted in Binding buffer such that the addition of 50 microliters/well gives a final concentration of 0.1 nM $[^{125}I]$-MIP-1 beta). The plate was sealed and allowed to stand at room temperature for 4-6 h before being counted on a Packard TopCount. The percentage bound for the test article was calculated, using negative and positive controls to define the window for each experiment.

Fluorometric Imaging Plate Reader (FLIPR)-Based

Functional assay: HT1080 cells (clone 3559.1.6) were plated at 10,000 cells/well (30 microliters) in 384-well plates (black/clear bottom Biocoat PDL, Beckton Dickinson) and charged with 30 microliters/well of Fluro-4 AM fluorescent dye (prepared by dissolving 1 mg Fluro-4 AM in 440 microliters DMSO and diluting with 100 microliters of pluronic solution before diluting further with 10 mL of Hanks buffer). The cells were incubated at 37° C. with 5% $CO_2$ for 30 min before being washed three times and suspended in Assay Buffer (20 mM HEPES, 1.2 mM $CaCl_2$, 5 mM $MgCl_2$, 2.5 mM Probenecid, 0.5% BSA, 1× Hanks). The test article was serially diluted in DMSO and then diluted 1:10 with Assay Buffer before being added to the cells (10 microliters/well).

Using FLIPR, the plates were read (10-70 sec) for induction of flux (i.e. agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR for one minute. Antagonist activity of the test article was determined relative to 0.4% DMSO/Buffer negative control.

The compounds of the present invention are inhibitors of both CCR2 and CCR5 and may be used to treat diseases associated with either chemokine.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurism, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes melitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field. Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:
1. A compound Formula (I)

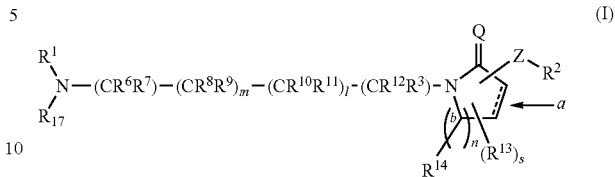

or a stereoisomer or a pharmaceutically acceptable salt thereof, wherein:

Z is $NR^{18}C(O)$—;

Q is selected from O and S;

wherein neither Z nor $R^{13}$ are connected to a carbon atom labeled (b);

bond (a) is a single bond;

$R^1$ is selected from H and $C_{1-6}$ alkyl;

$R^2$ is phenyl substituted with 0-5 $R^5$;

$R^3$ is $(CRR)_qOH$;

R is selected from H, methyl, ethyl, propyl, i-propyl, butyl, i-butyl, s-butyl, pentyl, neopentyl, and $(CH2)_r$phenyl substituted with 0-1 $R^{3e}$;

$R^{3e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{3f}R^{3f}$, $(CH_2)_rC(O)NHR^{3h}$, $(CH_2)_rOC(O)NHR^{3h}$, $(CH_2)_rOH$, $(CH_2)_rC(O)OH$, $(CH_2)_rC(O)OR^{3h}$, $(CH_2)_rC(O)NHSO_2$—$R^{3h}$, $NHSO_2R^{3h}$, a $(CH_2)_r$-5-6 membered heterocyclic system containing 1-4 heteroatoms selected from N, O, and S, and $(CH_2)_r$phenyl;

$R^{3f}$, at each occurrence, is selected from H, $C_{1-6}$ alkyl, and $C_{3-6}$ cycloalkyl;

$R^{3h}$, at each occurrence, is selected from $C_{1-5}$ alkyl, $C_{1-5}$ haloalkyl, $C_{3-6}$ cycloalkyl, and phenyl;

$R^5$ is selected from methyl, ethyl, propyl, i-propyl, butyl, i-butyl, s-butyl, pentyl, hexyl, $CF_3$, $CF_2CF_3$, $CF_2H$, $OCF_3$, Cl, Br, I, F, $SCF_3$, $NR^{5a}R^{5a}$, $NHC(O)OR^{5a}$, $NHC(O)R^{5b}$, and $NHC(O)NHR^{5a}$;

$R^{5a}$, at each occurrence, is independently selected from H, methyl, ethyl, propyl, i-propyl, butyl, s-butyl, i-butyl, t-butyl, pentyl, hexyl, allyl, propargyl, and a $(CH_2)_r$-$C_{3-10}$ carbocyclic residue substituted with 0-1 $R^{5e}$, wherein the carbocyclic residue is selected from cyclopropyl, cyclobutyl, cyclopentyl, cyclohexyl, phenyl and naphthyl;

$R^{5b}$, at each occurrence, is selected from methyl, ethyl, propyl, i-propyl, butyl, s-butyl, i-butyl, t-butyl, pentyl, hexyl, allyl, propargyl, a $(CH_2)_r$-$C_{3-6}$ carbocyclic residue selected from cyclopropyl, cyclobutyl, cyclopentyl, cyclohexyl, and phenyl; and a $(CH_2)_r$-5-6 membered heterocyclic system containing 1-4 heteroatoms selected from N, O, and S, wherein the heterocyclic system is selected from pyridinyl, thiophenyl, furanyl, indazolyl, azetidinyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, morphlinyl, piperidinyl, pyrrolyl, 2,5-dihydropyrrolyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, $(CH_2)_rOH$, OH, SH, C(O)OH, $C(O)NHR^{5h}$, $C(O)OC_{1-5}$ alkyl, $(CH_2)_rSC_{1-5}$ alkyl, $(CH_2)_rNR^{5f}R^{5f}$, $(CH_2)_rC(O)NHSO_2—R^{5h}$, $NHSO_2R^{5h}$, $(CH_2)_r$phenyl, and $(CH_2)$-tetrazolyl; and $R^{5f}$ at each occurrence, is selected from H, methyl, ethyl, propyl, i-propyl, butyl, cyclopropyl, cyclobutyl, and phenyl.

$R^{5h}$, at each occurrence, is selected from $C_{1-5}$ alkyl, $C_{1-5}$ haloalkyl, $C_{3-6}$ cycloalkyl, and phenyl;

$R^6$ is selected from H, methyl, ethyl, propyl, i-propyl, butyl, and t-butyl;

$R^7$ is H;

$R^9$ and $R^{11}$ are H;

$R^8$ and $R^{10}$ are independently selected from H, methyl, ethyl, propyl, i-propyl, and butyl;

$R^{12}$ is H;

$R^{13}$, at each occurrence, is independently selected from H, and $C_{1-4}$ alkyl substituted with 0-1 $R^{13b}$, —OH, —$NH_2$, F, Cl, Br, I, —$OR^{13c}$, —$N(R^{13c})_2$, or $C_{1-4}$ alkyl substituted with 0-3 $R^{13b}$;

$R^{13b}$, at each occurrence, is independently selected from —OH, —SH, —$NR^{13c}R^{13c}$, $C(O)NR^{13c}R^{13c}$, and —$NHC(O)R^{13c}$;

$R^{13c}$ is selected from H, $C_{1-4}$ alkyl and $C_{3-6}$ cycloalkyl;

$R^{14}$ is independently selected from H and $C_{1-4}$alkyl;

$R^{17}$ is selected from H and methyl;

$R^{18}$ is selected from H and $C_{1-4}$ alkyl;

n is 1;

m is 0;

s is 0 or 1;

r is 0, 1 or 2; and q is 1.

2. A pharmaceutical composition, comprising a pharmaceutically acceptable carrier and a therapeutically effective amount of a compound of claim 1.

* * * * *

UNITED STATES PATENT AND TRADEMARK OFFICE
CERTIFICATE OF CORRECTION

| | | |
|---|---|---|
| PATENT NO. | : 7,863,317 B2 | Page 1 of 1 |
| APPLICATION NO. | : 11/675213 | |
| DATED | : January 4, 2011 | |
| INVENTOR(S) | : Percy H. Carter | |

It is certified that error appears in the above-identified patent and that said Letters Patent is hereby corrected as shown below:

In the Claims:

Column 56
Claim 1, Line 2, after "compound" insert -- of --.

Column 57
Claim 1, Line 8, "$R^{5f}at$" should read -- $R^{5f}$, at --.

Column 58
Claim 1, Line 13, below "m is 0;" insert -- 1 is 0; --.

Signed and Sealed this
Fifteenth Day of May, 2012

David J. Kappos
*Director of the United States Patent and Trademark Office*